US012303902B2

(12) United States Patent
Fletcher et al.

(10) Patent No.: US 12,303,902 B2
(45) Date of Patent: May 20, 2025

(54) POINT-OF-CARE DIAGNOSTIC SYSTEMS AND CONTAINERS FOR SAME

(71) Applicant: IDEXX Laboratories, Inc., Westbrook, ME (US)

(72) Inventors: Michael Fletcher, Portland, ME (US); David L. Connolly, Eliot, ME (US); Anne Leavitt, Gorham, ME (US); Matthew M. Furtney, Freeport, ME (US); Christopher Labak, Brookline, NH (US); Christopher Aiston, Mont Vernon, NH (US); Daniel O'Sullivan, Mont Vernon, NH (US)

(73) Assignee: IDEXX LABORATORIES INC., Westbrook, ME (US)

( * ) Notice: Subject to any disclaimer, the term of this patent is extended or adjusted under 35 U.S.C. 154(b) by 140 days.

(21) Appl. No.: 17/836,474

(22) Filed: Jun. 9, 2022

(65) Prior Publication Data

US 2022/0339631 A1    Oct. 27, 2022

Related U.S. Application Data

(63) Continuation of application No. 16/378,483, filed on Apr. 8, 2019, now Pat. No. 11,358,148, which is a
(Continued)

(51) Int. Cl.
*B01L 3/00* (2006.01)
*G01N 35/10* (2006.01)

(52) U.S. Cl.
CPC ............. *B01L 3/523* (2013.01); *B01L 3/527* (2013.01); *B01L 2200/026* (2013.01); *G01N 35/10* (2013.01)

(58) Field of Classification Search
CPC .... B01L 3/523; B01L 3/527; B01L 2200/026; G01N 35/10; A61B 5/150389; A61B 5/15003
See application file for complete search history.

(56) References Cited

U.S. PATENT DOCUMENTS 3,909,136 A    9/1975    Thomas
4,387,164 A    6/1983    Hevey et al.
(Continued)

FOREIGN PATENT DOCUMENTS

EP    0284024 A2    9/1988
EP    2194385 A1    6/2010
(Continued)

OTHER PUBLICATIONS

Office Action issued in corresponding CA Application No. 3,095,051 dated Jun. 2, 2022, pp. 1-5.
(Continued)

*Primary Examiner* — John McGuirk
(74) *Attorney, Agent, or Firm* — Carter, DeLuca & Farrell LLP

(57) ABSTRACT

The present disclosure relates to a medical diagnostic system. In various embodiments, the system includes a housing, a first receptacle in the housing for receiving a reagent container, a second receptacle in the housing for receiving a working fluid and waste container, where the second receptacle is larger than the first receptacle, two reagent access needles positioned and fixed within the first receptacle with each of the two reagent access needles being positioned to access the reagent container, and a working fluid access needle and a waste access needle positioned and fixed within the second receptacle with the working fluid access needle and the waste access needle being positioned to access the working fluid and waste container.

18 Claims, 31 Drawing Sheets

Related U.S. Application Data continuation-in-part of application No. 15/941,596, filed on Mar. 30, 2018, now Pat. No. 11,541,396.

(56)     References Cited

U.S. PATENT DOCUMENTS

| | | | |
|---|---|---|---|
| 5,074,658 | A | 12/1991 | Tavlarides et al. |
| 5,171,538 | A | 12/1992 | Tremmel et al. |
| 5,262,329 | A | 11/1993 | Carver, Jr. |
| 5,316,725 | A | 5/1994 | Carver, Jr. et al. |
| 5,316,951 | A | 5/1994 | Carver, Jr. et al. |
| 5,380,491 | A | 1/1995 | Carver, Jr. et al. |
| 5,413,732 | A | 5/1995 | Buhl et al. |
| 5,463,228 | A | 10/1995 | Krause |
| 5,486,477 | A | 1/1996 | Carver, Jr. |
| 5,728,351 | A | 3/1998 | Carver, Jr. |
| 5,840,254 | A | 11/1998 | Carver, Jr. et al. |
| 6,391,263 | B1 | 5/2002 | Mishima et al. |
| 6,812,032 | B1 | 11/2004 | Carver, Jr. et al. |
| 6,857,530 | B2 | 2/2005 | Yourist |
| 6,887,429 | B1 | 5/2005 | Marshall et al. |
| 6,979,569 | B1 | 12/2005 | Carver, Jr. et al. |
| 7,294,307 | B2 | 11/2007 | Carver, Jr. |
| 7,324,194 | B2 | 1/2008 | Roche et al. |
| 7,499,581 | B2 | 3/2009 | Tribble et al. |
| 7,873,483 | B2 | 1/2011 | Miyamoto et al. |
| 7,982,201 | B2 | 7/2011 | Bryant et al. |
| 8,086,411 | B2 | 12/2011 | Yoshida et al. |
| 8,088,593 | B2 | 1/2012 | Burd et al. |
| 8,161,810 | B2 | 4/2012 | Cadieux et al. |
| 8,381,581 | B2 | 2/2013 | Walsh et al. |
| 8,460,528 | B2 | 6/2013 | Pollack et al. |
| 8,668,869 | B2 | 3/2014 | Hirayama |
| 8,679,425 | B2 | 3/2014 | Ueda et al. |
| 9,213,043 | B2 | 12/2015 | Cook et al. |
| 9,222,821 | B2 | 12/2015 | Walsh et al. |
| 9,233,371 | B2 | 1/2016 | Nakamura et al. |
| 9,322,834 | B2 | 4/2016 | Hirayama et al. |
| 2002/0004650 | A1* | 1/2002 | Kuracina .......... A61M 25/0625 128/919 |
| 2005/0074361 | A1 | 4/2005 | Tanoshima et al. |
| 2006/0105359 | A1 | 5/2006 | Favuzzi et al. |
| 2011/0014095 | A1 | 1/2011 | Ueda et al. |
| 2011/0014687 | A1 | 1/2011 | Nakamura et al. |
| 2011/0207621 | A1 | 8/2011 | Montagu et al. |
| 2012/0046203 | A1 | 2/2012 | Walsh et al. |
| 2012/0309636 | A1 | 12/2012 | Gibbons et al. |
| 2014/0027333 | A1* | 1/2014 | Pawlowski .............. A61J 1/14 248/346.03 |
| 2014/0267695 | A1 | 9/2014 | Scordato et al. |
| 2015/0074361 | A1 | 3/2015 | Hughes et al. |
| 2015/0316529 | A1 | 11/2015 | Choi et al. |
| 2015/0362459 | A1 | 12/2015 | Chung et al. |
| 2016/0184826 | A1 | 6/2016 | Nemoto et al. |
| 2016/0266155 | A1 | 9/2016 | Brennan et al. |
| 2016/0318022 | A1 | 11/2016 | Accurso |
| 2017/0122846 | A1 | 5/2017 | Holmes et al. |
| 2017/0246623 | A1 | 8/2017 | Magnusson |
| 2019/0000365 | A1 | 1/2019 | Beyerlein et al. |
| 2019/0120869 | A1 | 4/2019 | Belz et al. |
| 2020/0337620 | A1 | 10/2020 | Morrison et al. |

FOREIGN PATENT DOCUMENTS

| | | |
|---|---|---|
| JP | S6242334 A | 2/1987 |
| JP | H03176664 A | 7/1991 |
| JP | 2008203277 A | 9/2008 |
| JP | 2011039028 A | 2/2011 |
| JP | 2016540221 A | 12/2016 |
| WO | 2013173524 A2 | 11/2013 |

OTHER PUBLICATIONS

Australian Examination Report No. 1 issued in corresponding Appl. No. AU 2019245325 dated Nov. 16, 2020 (6 pages).

International Search Report and Written Opinion issued by the European Patent Office acting as International Searching Authority in corresponding International Application No. PCT/US2019/026405 on Jul. 18, 2019.

Partial International Search Report issued by the European Patent Office acting as the International Searching Authority on May 21, 2019 in corresponding International Application No. PCT/US2019/026405.

Office Action issued in corresponding JP Application No. 2020-552896, dated Nov. 30, 2021, pp. 1-8, together with English-language translation.

Examination Report No. 1 issued in corresponding AU Patent Application No. 2022201154, dated Apr. 5, 2023, pp. 1-3.

Rejection Decision issued in corresponding CN Patent Application No. 201980017943.6, dated Mar. 31, 2023, pp. 1-16, with English translation.

Brazilian Office Action issued in corresponding BR Application No. 112020016186-1 dated Dec. 13, 2022, pp. 1-6, with partial English translation.

Notice of Reasons for Refusal issued by the Japanese Patent Office on Mar. 12, 2024 in corresponding JP Patent Application No. 2023-106080, with English translation.

Examination Report issued by the European Patent Office in corresponding EP Patent Application No. 19719053.1, dated Feb. 28, 2024, pp. 1-5.

Office Action issued in corresponding CN Application No. 201980017943.6 dated Jul. 1, 2022, pp. 1-17.

Office Action issued by the Mexican Institute of Industrial Property (MIIP) on Jun. 28, 2024 in corresponding MX Patent Application No. MX/a/2020/010054, with partial English translation.

* cited by examiner

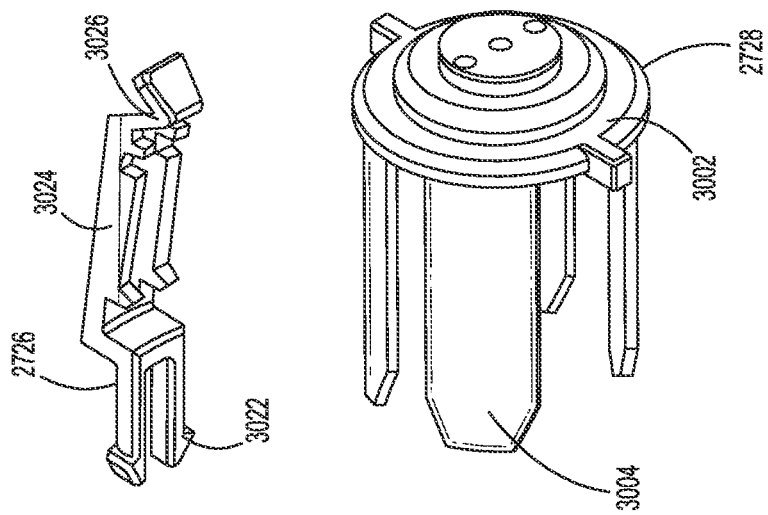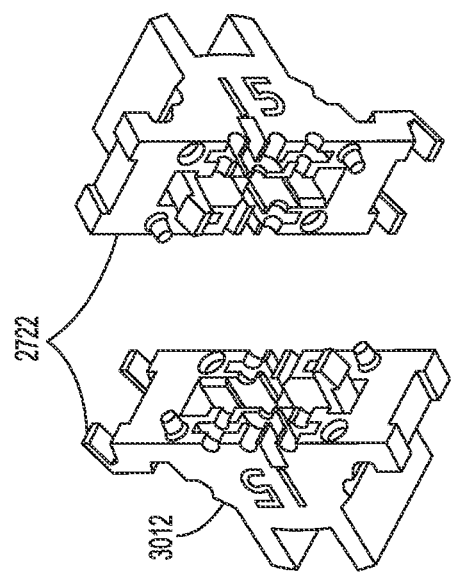
FIG. 30

POINT-OF-CARE DIAGNOSTIC SYSTEMS AND CONTAINERS FOR SAME

CROSS-REFERENCE TO RELATED APPLICATIONS

The present application is a continuation of U.S. patent application Ser. No. 16/378,483, filed Apr. 8, 2019, which is a continuation-in-part of U.S. patent application Ser. No. 15/941,596, filed Mar. 30, 2018. The entire contents of each of the foregoing applications are hereby incorporated by reference herein.

TECHNICAL FIELD

The present disclosure relates to medical diagnostics, and more particularly, to point-of-care medical diagnostic systems.

BACKGROUND

Medical guidance for many medical diagnostic systems, such as hematology analyzers, recommends analyzing a sample as soon as possible after drawing the sample. This recommendation can be difficult if the sample is obtained at the point of care but the test is to be performed at an external laboratory. Therefore, many doctors and veterinarians prefer to have point-of-care (POC) systems to analyze fresh samples.

POC medical diagnostic systems use various types of reagents and fluids to perform their analyses. Various types of packages exist for the reagents and fluids, and such packages must be delivered to and installed by the POC offices. Installations requiring a multitude of steps can confuse and frustrate operators. In some cases, POC diagnostic systems may still operate even if packages are improperly installed but may produce incorrect results. Accordingly, there is continuing interest in improving POC medical diagnostic systems and reagent and fluid packages for POC medical diagnostic systems.

SUMMARY

The present disclosure relates to point-of-care medical diagnostic systems and containers for such systems.

In accordance with aspects of the present disclosure, a medical diagnostic system includes a housing, a first receptacle in the housing for receiving a reagent container, a second receptacle in the housing for receiving a working fluid and waste container where the second receptacle is larger than the first receptacle, two reagent access needles positioned and fixed within the first receptacle with each of the two reagent access needles being positioned to access the reagent container, and a working fluid access needle and a waste access needle positioned and fixed within the second receptacle with the working fluid access needle and the waste access needle being positioned to access the working fluid and waste container.

In various embodiments, the first receptacle includes a top wall, a bottom wall, side walls, and a back wall. One of the two reagent access needles is positioned on the back wall adjacent to the bottom wall. The other of the two reagent access needles is positioned on the back wall adjacent to and above a center line between the top and bottom walls. In various embodiments, the reagent container and the first receptacle are shaped such that the reagent container must be inserted into the first receptacle in a particular orientation for the two reagent access needles to access the reagent container.

In various embodiments, the second receptacle includes a top wall, a bottom wall, side walls, and a back wall. The waste access needle is positioned on the back wall adjacent to the top wall. The working fluid access needle is positioned on the back wall adjacent to the bottom wall. In various embodiments, the working fluid and waste container and the second receptacle are shaped such that the working fluid and waste container must be inserted into the second receptacle in a particular orientation for the working fluid access needle and the waste access needle to access the working fluid and waste container. In various embodiments, a top portion of the second receptacle is narrower than a bottom portion of the second receptacle, and a top portion of the working fluid and waste container is narrower than a bottom portion of the working fluid and waste container.

In various embodiments, the medical diagnostic system includes a camera positioned such that it can view the first receptacle for imaging an encoded data-matrix code on the reagent container. In various embodiments, the medical diagnostic system uses the same camera positioned such that it can also view the second receptacle for imaging an encoded data-matrix code on the working fluid and waste container.

In various embodiments, the reagent container of the medical diagnostic system includes a top compartment and a bottom compartment that are fluidically separate. A septum between the top and bottom compartments connects them such that the top and bottom compartments are stationary relative to each other. The top compartment is defined by a housing having a top wall, a bottom wall, side walls, and an access opening positioned adjacent to the bottom wall of the top compartment. The bottom compartment is defined by a housing having a top wall, a bottom wall, side walls, and an access opening positioned adjacent to the bottom wall of the bottom compartment. In various embodiments, at least a portion of the bottom wall of the top compartment slopes downward toward the access opening of the top compartment. In various embodiments, the top wall of the bottom compartment is substantially parallel to the bottom wall of the top compartment. In various embodiments, a portion of the top wall of the bottom compartment is higher than a portion of the bottom wall of the top compartment.

In various embodiments, the working fluid and waste container of the medical diagnostic system includes a working fluid compartment having an access opening, a waste compartment having an access opening where the waste compartment is fluidically separate from the working fluid compartment, and a septum between and connecting the working fluid compartment and the waste compartment such that the working fluid compartment and the waste compartment are stationary relative to each other. In various embodiments, the second receptacle of the housing includes a top wall, a bottom wall, side walls, and a back wall. The access opening of the waste compartment is positioned adjacent to the top wall of the second receptacle, and the access opening of the working fluid compartment is positioned adjacent to the bottom wall of the second receptacle. In various embodiments, the waste compartment has an inner wall and an outer wall. The inner wall and the outer wall have a vertical cross-section in substantially a shape of a trapezoid with an open corner. The working fluid compartment has a first portion inward of the inner wall of the waste compartment and a second portion extending through the open corner where the second portion ends in the access opening of the working fluid compartment.

In accordance with aspects of the present disclosure, a container for a medical diagnostics system includes a top compartment defined by a housing having a top wall, a bottom wall, side walls, and an access opening positioned adjacent to the bottom wall of the top compartment, a bottom compartment defined by a housing having a top wall, a bottom wall, side walls, and an access opening positioned adjacent to the bottom wall of the bottom compartment, where the top compartment and the bottom compartment are fluidically separate, and a septum between and connecting the top and bottom compartments such that the top and bottom compartments are stationary relative to each other.

In various embodiments, at least a portion of the bottom wall of the top compartment slopes downward toward the access opening of the top compartment. In various embodiments, the top wall of the bottom compartment is substantially parallel to the bottom wall of the top compartment.

In accordance with aspects of the present disclosure, a container for a medical diagnostics system includes a waste compartment having an access opening, an inner wall, and an outer wall, where the inner wall and the outer wall have a vertical cross-section in substantially a shape of a trapezoid with an open corner, a working fluid compartment having a first portion inward of the inner wall of the waste compartment and a second portion extending through the open corner, where the second portion ends in an access opening of the working fluid compartment and where the working fluid compartment is fluidically separate from the waste compartment, and a septum between and connecting the working fluid compartment and the waste compartment such that the working fluid compartment and the waste compartment are stationary relative to each other.

In various embodiments, the container is configured to fit into a receptacle having a top wall, a bottom wall, side walls, and a back wall, the access opening of the waste compartment is positioned adjacent to the top wall of the receptacle, and the access opening of the working fluid compartment is positioned adjacent to the bottom wall of the receptacle.

In accordance with aspects of the present disclosure, a medical diagnostic system includes a housing, a receptacle in the housing for receiving a container having a compartment where the receptacle includes a wall, and a compartment engagement mechanism for engaging the compartment. The compartment engagement mechanism includes a hub fixed within the wall of the receptacle, at least one needle secured to the hub, a needle cover slideably coupled with the hub and having a cover position that covers the needle, and at least one engagement arm secured to the hub and grasping the needle cover when the needle cover is in the cover position.

In various embodiments, the at least one needle includes a coated needle and at least one non-coated needle.

In various embodiments, the needle cover includes a cap having at least one aperture corresponding to the at least one needle, and a plurality of glide posts slideably coupled with the hub, wherein the at least one needle protrudes through the at least one aperture of the cap when the plurality of glide posts slides into the hub.

In various embodiments, the at least one engagement arm includes a base portion secured to the hub, an elbow portion connected to the base portion, and a grasping portion connected to the elbow portion, where the elbow portion is semi-flexible and permits the grasping portion to move radially closer to and away from the needle cover.

In various embodiments, the medical diagnostic system further includes the container, where the container includes a cap secured to a neck of the compartment, and the cap is sized to contact the grasping portion of the at least one engagement arm and move the grasping portion radially away from the needle cover when the compartment engagement mechanism engages the compartment of the container.

In various embodiments, the compartment includes a collar having at least one notch corresponding to the at least one engagement arm, where the at least one notch of the collar receives the grasping portion of at least one engagement arm when the compartment of the container is fully engaged with the compartment engagement mechanism.

In various embodiments, the container includes a second compartment having a second neck and a second cap secured to the second neck, and the medical diagnostic system further includes a second compartment engagement mechanism coupled to the wall of the receptacle for engaging the second compartment of the container.

In various embodiments, the medical diagnostic system further includes a level detection mechanism coupled to the compartment engagement mechanism and the second compartment engagement mechanism, where the level detection mechanism detects whether the container is level within the receptacle.

In various embodiments, the compartment engagement mechanism is a different size from the second compartment engagement mechanism, and the cap is a different size from the second cap. In various embodiments, the compartment engagement mechanism and the second compartment engagement mechanism extend different distances from the wall of the receptacle, and the cap and the second cap extend different distances from a body of the container.

Further details and aspects of exemplary embodiments of the present disclosure are described in more detail below with reference to the appended figures.

BRIEF DESCRIPTION OF THE DRAWINGS

FIG. 30 is a diagram of certain components of the compartment engagement mechanism of FIG. 27, in accordance with aspects of the present disclosure;

DETAILED DESCRIPTION

Figure 1:
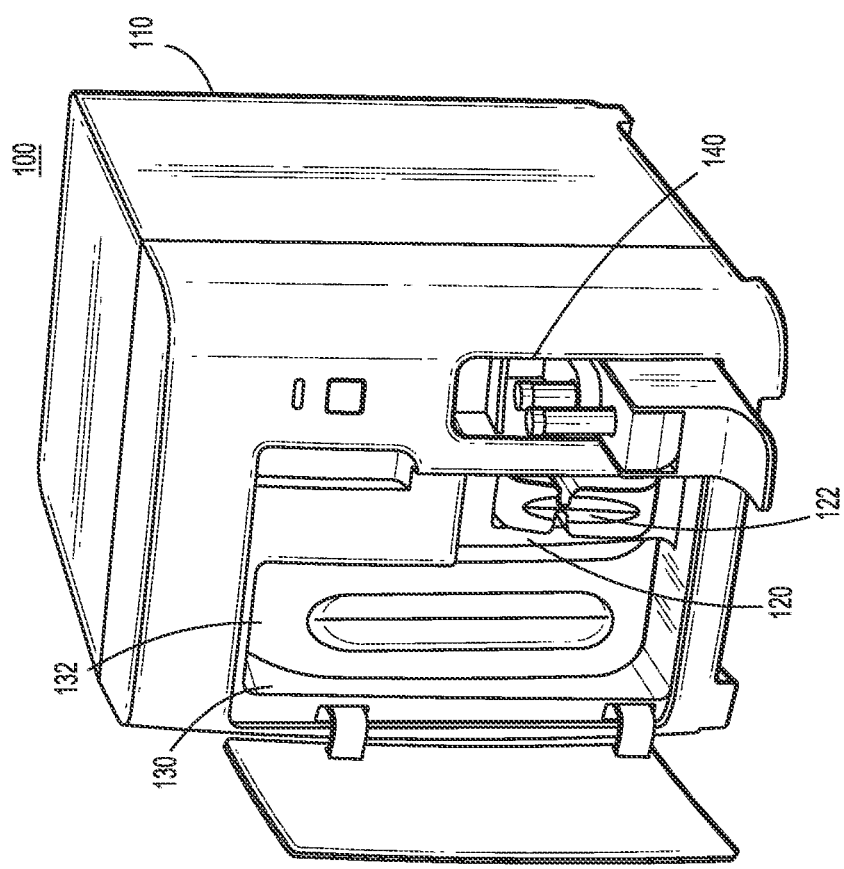
FIG. 1 is a diagram of an embodiment of a medical diagnostic system in accordance with aspects of the present disclosure.

The present disclosure relates to point-of-care medical diagnostic systems and containers for medical diagnostic systems. As used herein, point-of-care refers to a location where care is provided to human or animal patients, and a medical diagnostic system refers to a system that can analyze a sample obtained from a patient to diagnose a medical condition of the patient. Accordingly, a medical diagnostic system includes a patient sample analyzer, such as, but not limited to, a flow cytometer.

The following description will use flow-cytometry-based systems as an example of a medical diagnostic system. An example of a flow-cytometry-based analyzer is shown and described in U.S. Pat. No. 7,324,194, which is hereby incorporated by reference herein in its entirety, and which persons skilled in the art will understand. The present disclosure, however, is intended to and should be understood to apply to other types of medical diagnostic systems as well.

Flow cytometry systems include sub-systems such as fluidics, optics, and electronics sub-systems. A fluidics sub-system arranges a sample into a stream of particles, such as a stream of cells. The optics sub-system examines each cell by directed a laser beam to each cell and detecting scattered light using photo-detectors. Light is scattered according to size, complexity, granularity, and diameter of the cells, which form a "fingerprint" of each cell type. The electronics sub-system can process the fingerprints to classify, count, and/or otherwise analyze the cells/particles in the sample stream.

The fluidics sub-system has many responsibilities. For example, the fluidics sub-system uses a working fluid in various ways, including transporting dilutions (blood or quality control materials) to a laser for cell counting and morphology and/or to a hemoglobin module for hemoglobin measurement, acting as a sheath to carry blood cells sequentially past the laser, cleaning and/or priming the diagnostic system, and/or carrying waste to a waste container. The working fluid material is typically water-based and contains salt, surfactants, buffers and antimicrobials. The fluidic system is generally filled with this fluid at all times, except when a blood sample is being processed and moved through the system.

The fluidics sub-system also accesses reagents and applies them to the patient sample to produce desired reactions. For example, as persons skilled in the art will understand, reagents can be used to dye and distinguish particular cells, lyse red blood cells, and prepare cells for particular types of assays, among other things. In various embodiments, a red reagent is used to prepare a whole blood sample for evaluation primarily of red blood cells and platelets. The material is water-based and contains salt, surfactants, antimicrobials, and a stain (for reticulocytes). The red reagent is mixed in the proper dilution concentration with whole blood to cause the red blood cells to sphere and to stain the reticulocytes. The diluted sample is then transported to the flow cell for evaluation (counting and classification). In various embodiments, a white reagent is used to prepare a whole blood sample for evaluation of white blood cells. The material is water-based and contains salt, surfactants, and antimicrobials. The white reagent is mixed in the proper dilution concentration with whole blood to cause the red blood cells to lyse. The remaining white blood cells and platelets are left in the dilution and are transported to the flow cell for evaluation (counting and classification).

Accordingly, working fluid and reagents need to be installed and provided to the medical diagnostic system. Then, when the analysis is completed, waste fluids generated by the system need to be gathered and disposed in a safe manner. The following describe a medical diagnostic system and containers that address these concerns.

Referring now to FIG. 1, there is shown an exemplary medical diagnostic system 100. The illustrated medical diagnostic system 100 is configured and sized to reside within a point-of-care (POC) office. The illustrated system includes a housing 110 that forms the overall structure of the medical diagnostic system. The housing 110 includes a smaller receptacle 120 that is intended to receive a reagent container 122 and a larger receptacle 130 that is intended to receive a working fluid and waste container 132. The reagent container 122 stores reagents that will be used by the diagnostic system 100, and the working fluid and waste container 132 operates to provide working fluid to the diagnostic system 100 and to receive waste fluid from the diagnostic system 100. At the right side of the housing 110, another receptacle 140 can receive various fluids and materials, including a patient sample, system cleaning fluid, and quality control materials, among other things.

As will be described in more detail below, the receptacles 120, 130 and the containers 122, 132 are configured so that an operator can slide a container 122, 132 into a receptacle. In accordance with one aspect of the present disclosure, the interiors of the receptacles 120, 130 include fluid access needles (not shown). As the containers 122, 132 slide into the receptacles 120, 130, the needles engage access openings in the containers. In various embodiments, one or both of the receptacles 120, 130 is horizontal or substantially horizontal such that an operator can slide a container 122, 132 horizontally into a receptacle, and the fluid access needles (not shown) can also be oriented horizontally or have a substantially horizontal orientation. As used herein, the term "horizontal" refers to an orientation that is parallel to a surface or plane on which the diagnostic system 100 is placed. In various embodiments, the receptacles and access needles are substantially horizontal in that they are intended to be horizontal but may not be fully horizontal due to, for example, slight manufacturing imperfections or limitations, or slight loosening of the needles within the receptacle over time due to wear, or other material, manufacturing, or environmental imperfections. In various embodiments, one or both of the receptacles 120, 130 are angled such that an operator can slide a container 122, 132 into a receptacle non-horizontally, such as at a downward angle, and the fluid access needles (not shown) can also be oriented at an angle. In various embodiments, one or more fluid access needles can be oriented parallel to the direction at which a container 122, 132 slides into a receptacle 120, 130. In various embodiments, one or more fluid access needles (not shown) can be oriented at an angle with respect to the direction at which a container 122, 132 slides into a receptacle 120, 130. Combinations of the disclosed embodiments are contemplated, such that each receptacle, container, or access needle can be implemented by a different disclosed embodiment.

Figure 2:
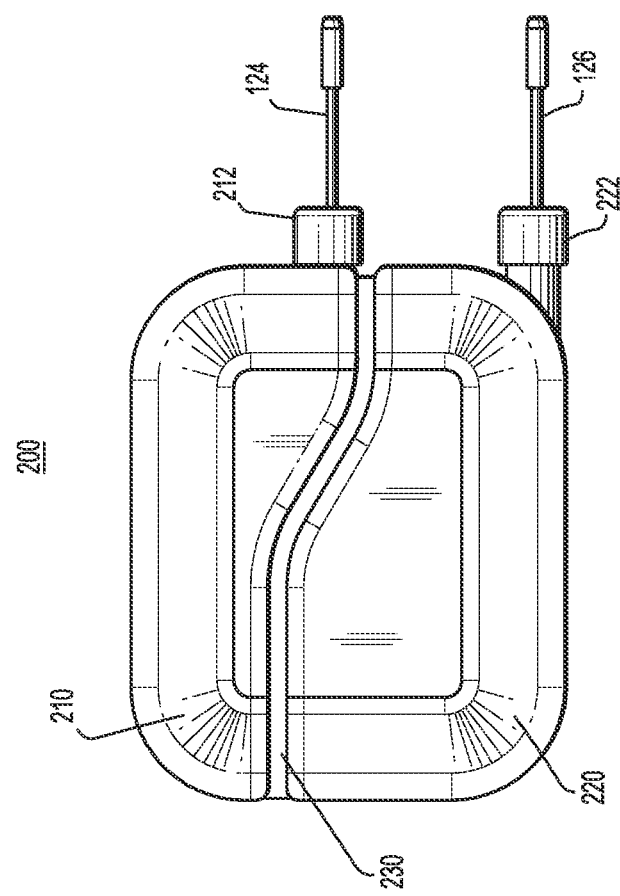
FIG. 2 is a diagram of an embodiment of a reagent container, in accordance with aspects of the present disclosure.

Referring now to FIG. 2, there is shown a side view of an exemplary reagent container 200. The reagent container includes a top compartment 210 and a bottom compartment 220. The two compartments 210, 220 are fluidically separate. A septum 230 between the top and bottom compartments 210, 220 connects the two compartments and holds them stationary relative to each other. In various embodiments, the reagent container is a single molded vessel, where the two compartments and the septum between the two compartments are formed in the same molding process. The top compartment 210 and the bottom compartment 220 both end with an access opening 212, 222. The access openings 212, 222 are positioned so that the reagent access needles 124, 126 located within the smaller receptacle 120 of the diagnostic system can access them. In various embodiments, the access openings can be covered by a fluid seal that prevents the reagents from spilling. The reagent access needles 124, 126 can puncture the fluid seal to access the reagents. The reagent access needles 124, 126 are illustrated for clarity and are not a part of the reagent container.

Figure 3:
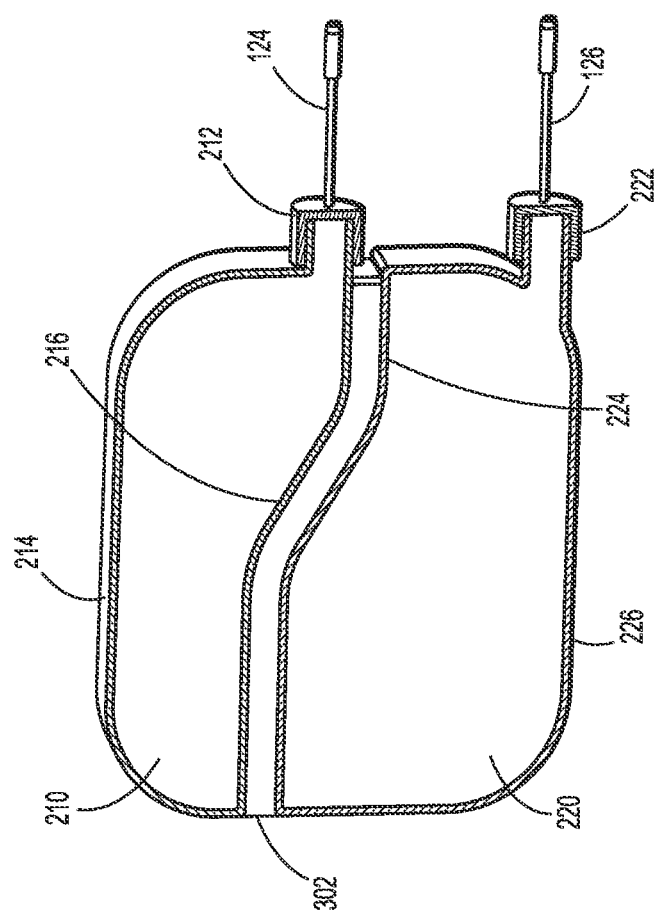
FIG. 3 is a diagram of a cross-section of the reagent container of FIG. 2, in accordance with aspects of the present disclosure.

FIG. 3 shows a vertical cross-section of the reagent container 200 of FIG. 2. The top compartment 210 includes a top wall 214 and a bottom wall 216, and the bottom compartment 220 includes a top wall 224 and a bottom wall 226. Side walls of the top and bottom compartments 210, 220 are illustrated in FIG. 2. Depending on the location of the vertical cross-section, the area 302 between the top compartment 210 and the bottom compartment 220 may be the septum 230 or may be empty space. For example, as shown in FIG. 1, the septum 230 is narrower than the widths of the top and bottom compartments 210, 220. If the vertical cross-section is taken over the septum 230, then the septum 230 will be in the area 302 between the top and bottom compartments. If the vertical cross-section is taken outside of the septum 230, then the area 302 between the top and bottom compartments 210, 220 will be air. In various embodiments, the septum 230 can be wider or narrower or another width than as illustrated in FIG. 1.

As shown in FIG. 3, the access openings 212, 222 of the top and bottom compartments 210, 220 are adjacent to the bottom walls 216, 226. The reagent access needles 124, 126 are positioned to insert into the bottom portion of the access openings 212, 222, so as to reach as much of the reagents as possible. A portion of the bottom wall 216 of the top compartment 210 slopes downward towards the access opening 212 of the top compartment. Thus, essentially all of the reagent in the top compartment 210 will be able to reach the access opening 212 and be accessed by the fluid access needle 124. In contrast, in the illustrated embodiment, the bottom compartment 220 does not include a slope at its bottom wall 226. Thus, some portion of the reagent in the bottom compartment 220 will be inaccessible to the fluid access needle 126. In various embodiments, the bottom wall 226 of the bottom compartment 220 can include a downward slope.

The particular shapes and relative sizes of the compartments are exemplary, and other variations and configurations are contemplated. For example, in the embodiment of FIGS. 2 and 3, the top compartment 210 is smaller than the bottom compartment 220. For example, the top compartment 210 may hold from about 60 mL to about 130 mL, from about 70 mL to about 120 mL, from about 80 mL to about 110 mL, from about 90 mL to about 100 mL, or, most preferably, about 95 mL of reagent; and the bottom compartment 220 may hold from about 175 mL to about 100 mL, from about 165 mL to about 110 mL, from about 155 mL to about 120 mL, from about 145 mL to about 130 mL, or, most preferably, about 139 mL of reagent. In various other embodiments, other capacities are contemplated, and other proportions of capacities between the top and bottom compartments 210, 220 are contemplated.

Figure 4:
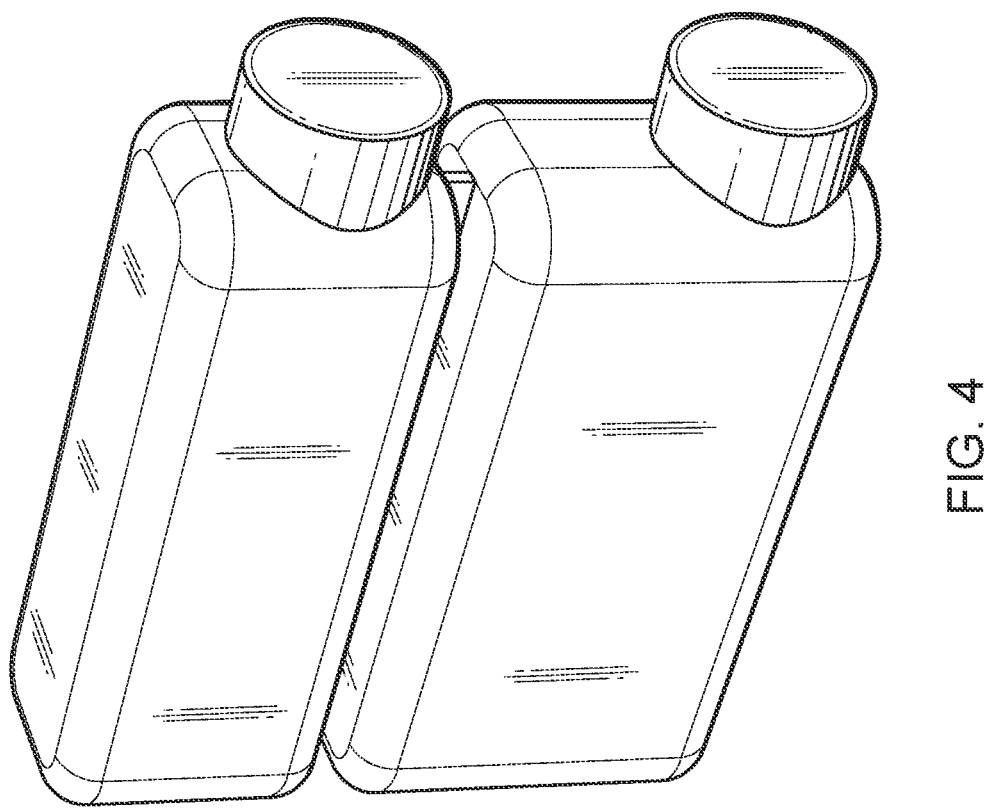
FIG. 4 is a diagram of another embodiment of a reagent container, in accordance with aspects of the present disclosure.

In the illustrated embodiment, the bottom wall 216 of the top compartment 210 and the top wall 224 of the bottom compartment 220 are parallel or substantially parallel. They may be substantially parallel even when they are intended to be entirely parallel because of, for example, manufacturing imperfections. In various other embodiments, the bottom wall 216 of the top compartment 210 and the top wall 224 of the bottom compartment 220 can be intentionally non-parallel. Additionally, in the illustrated embodiment, a portion of the top wall 224 of the bottom compartment 220 is higher than a portion of the bottom wall 216 of the top compartment 210 because of the downward slope in those walls. In various other embodiments, there may be no downward slope in those walls, such as in the example of FIG. 4.

In the illustrated embodiment, the septum 230 adjacent to the access openings 212, 222 is located about halfway between the top wall 214 of the top compartment 210 and the bottom wall 226 of the bottom compartment 220. Thus, the access opening 212 of the top compartment 210 is located adjacent to and above this center line. The reagent access needles 124, 126 are located in corresponding positions. The smaller receptacle 120 of the diagnostic system includes a top wall, a bottom wall, a back wall, and side walls (not shown). One reagent access needle 126 is positioned on the back wall adjacent to the bottom wall of the smaller receptacle 120, and the other reagent access needle 124 is positioned on the back wall adjacent to and above the center line between the top and bottom walls of the smaller receptacle 120 (not shown). Thus, the reagent access needles 124, 126 can access the compartments 210, 220 only when the reagent container 200 is inserted into the smaller receptacle 120 in a particular orientation. In various other embodiments, the locations of the access openings 212, 222 and the reagent access needles 124, 126 can be in other positions, as shown for example, in FIG. 4.

Described above herein are aspects of the medical diagnostic system and the reagent container. The following will describe aspects of the working fluid and waste container. As shown in FIG. 1, the working fluid and waste container 132 is larger than the reagent container 122. In various embodiments, other size proportions between the reagent container 122 and the working fluid and waste container 132 are contemplated.

Figure 5:
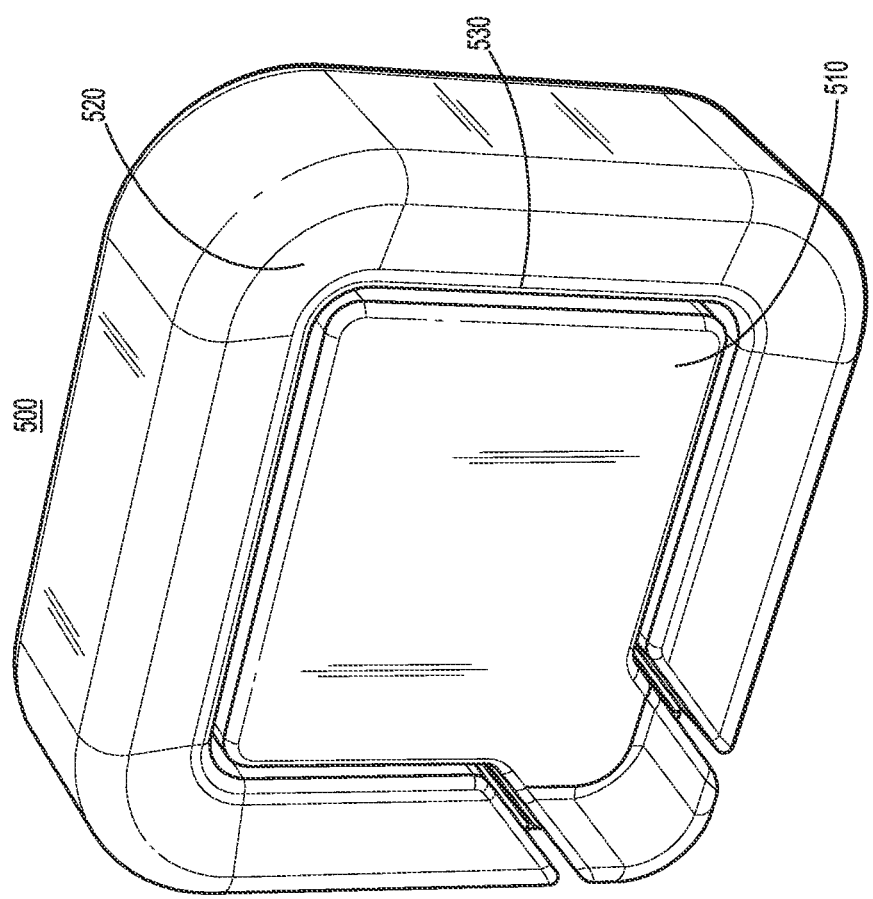
FIG. 5 is a diagram of an embodiment of a working fluid and waste container, in accordance with aspects of the present disclosure.
Figure 6:
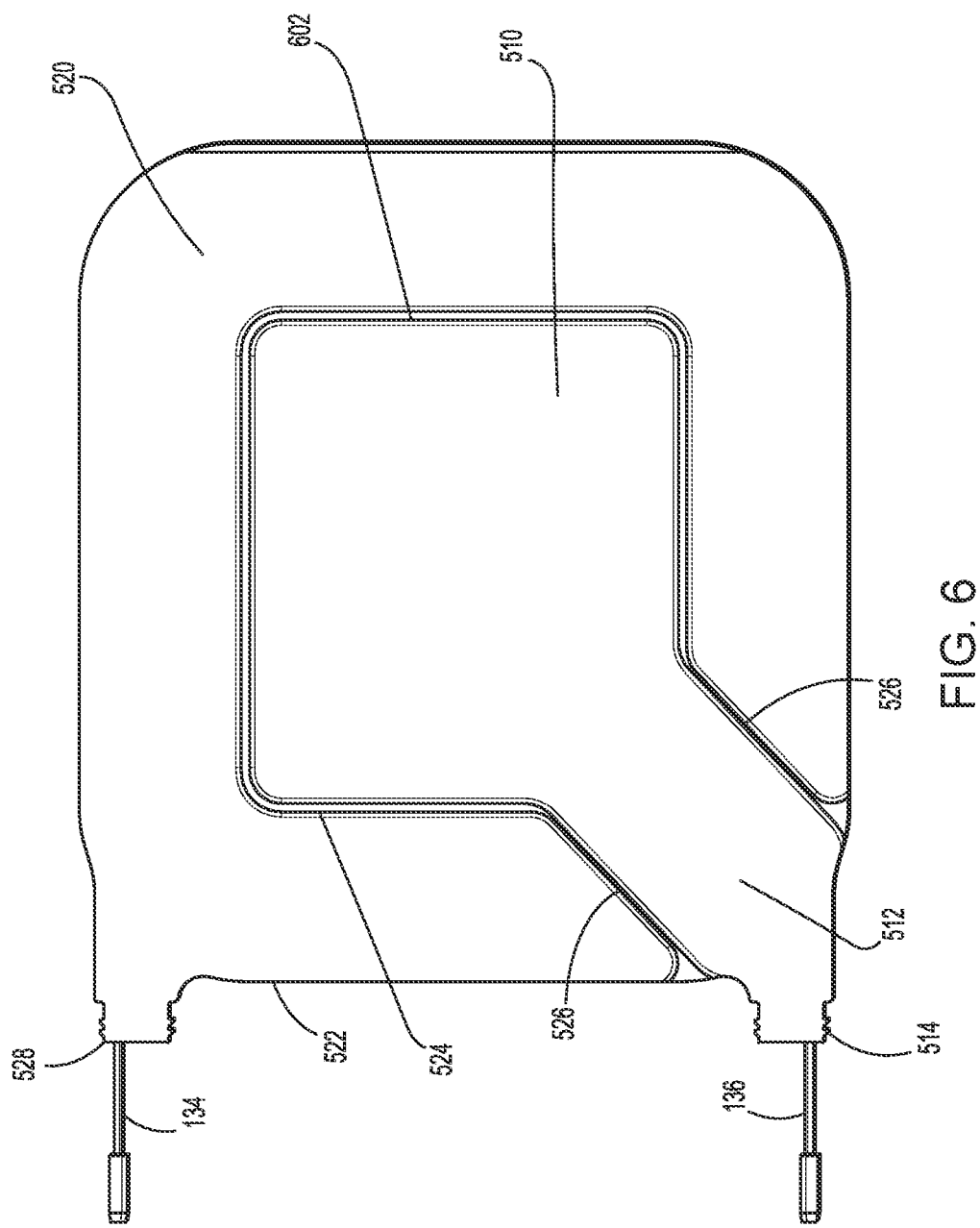
FIG. 6 is a diagram of a cross-section of the working fluid and waste container of FIG. 5, in accordance with aspects of the present disclosure.

Referring to FIG. 5, there is shown an embodiment of a working fluid and waste container 500 that includes a working fluid compartment 510 and a waste compartment 520. The working fluid and waste compartments 510, 520 are fluidically separate. A septum 530 is positioned between the compartments and connects them such that the working fluid and waste compartments 510, 520 are stationary relative to each other. In various embodiments, the working fluid and waste container is a single molded vessel, where the two compartments and the septum between the two compartments are formed in the same molding process. Referring also to FIG. 6, a vertical cross-section of the working fluid and waste container 500 of FIG. 5 is shown. Depending on the location of the vertical cross-section, the area 602 between the waste compartment 520 and the working fluid compartment 510 may be the septum 530 or may be empty space. For example, as shown in FIG. 5, the septum 530 is narrower than the widths of the working fluid and waste compartments 510, 520. If the vertical cross-section is taken over the septum 530, then the septum 530 will be in the area 602 between the working fluid and waste compartments 510, 520. If the vertical cross-section is taken outside of the septum 530, then the area 602 between the working fluid and waste compartments 510, 520 will be air. In various embodiments, the septum 530 can be wider or narrower or another width than as illustrated in FIG. 5.

With continuing reference to FIG. 6, the waste compartment 520 has an outer wall 522, an inner wall 524, and end walls 526 connecting the outer and inner walls 522, 524. The outer wall 522 and the inner wall 524 have vertical cross-sections that are substantially in the shape of a square or rectangle with an open corner. In various embodiments, the vertical cross-sections may have another shape or substantially another shape, such as a trapezoid. The cross-sections may have substantially a particular shape, but not exactly a particular shape, because of, for example, rounded corners or manufacturing imperfections or material stress over time. In various embodiments, the cross-sectional shape can be oriented in different directions. For example, when the cross-sectional shape is a trapezoid, the base of the trapezoid can be oriented towards any side of the waste compartment 520. The working fluid compartment 510 includes a portion that is within the inner wall 524 of the waste compartment 520 and another portion 512 that extends through the open corner of the waste compartment 520 and ends at an access opening 512.

With reference to the medical diagnostic system of FIG. 1, the working fluid and waste container 132 slides into the larger receptacle 130. The larger receptacle 130 includes a top wall, a bottom wall, a back wall, and side walls (not shown). With reference to the larger receptacle 130, the access opening 528 of the waste compartment 520 is positioned adjacent to the top wall of the larger receptacle 130, and the access opening 514 of the working fluid compartment 510 is positioned adjacent to the bottom wall of the second receptacle 130. The working fluid and waste access needles 134, 136 are located in corresponding positions. The waste access needle 134 is positioned on the back wall of the larger receptacle 130 adjacent to the top wall of the larger receptacle 130, and the working fluid access needle 136 is positioned on the back wall of the larger receptacle 130 adjacent to the bottom wall of the larger receptacle 130. In various embodiments, the working fluid access needle 136 is positioned towards the bottom portion of the access opening 514 for the working fluid compartment 510. In this manner, substantially all of the working fluid is accessible to the working fluid access needle 136. In various embodiments, the waste access needle 134 is positioned towards the top portion of the access opening 528 for the waste compartment 520. In this manner, the waste compartment 520 can be filled without the stale waste fluid in the waste compartment 520 contacting the waste access needle 134, thereby providing less risk of contaminating the waste access needle 134 or of backflow through the waste access needle 134. In various embodiments, the access openings 514, 528 can be covered by a fluid seal that prevents the fluid from spilling. The working fluid and waste access needles 134, 136 can puncture the fluid seal to access the interior of the compartments 510, 520.

Referring again to FIG. 1, in accordance with aspects of the present disclosure, the working fluid and waste container 132 and the larger receptacle 130 are shaped such that the working fluid and waste container 132 must be inserted into the larger receptacle 130 in a particular orientation for the working fluid access needle 136 and the waste access needle 134 to access the working fluid and waste container 132. In various embodiments, the top portion of the larger receptacle 130 is narrower than the bottom portion of the larger receptacle 130, and the top portion of the working fluid and waste container 132 is also narrower than the bottom portion of the working fluid and waste container 132. Thus, the working fluid and waste container 132 must be inserted in the correct orientation for the working fluid access needle 136 and the waste access needle 134 to access the access openings of the working fluid and waste container 130.

The working fluid and waste container of FIGS. 5 and 6 is exemplary, and other shapes and configurations are contemplated to be within the scope of the present disclosure. For example, other embodiments of the working fluid and waste container are shown in FIGS. 7-10.

Figure 7:
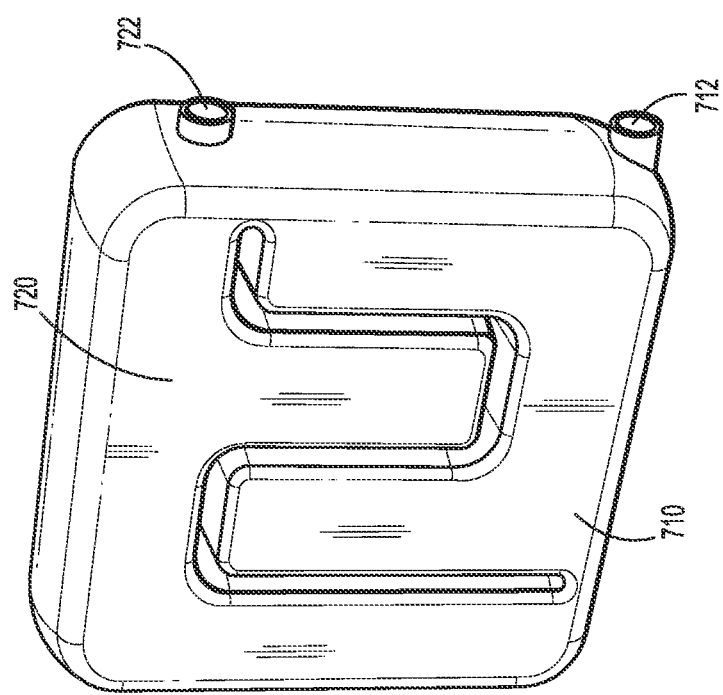
FIG. 7 is a diagram of another embodiment of a working fluid and waste container, in accordance with aspects of the present disclosure.

In the embodiment of FIG. 7, the working fluid compartment 710 has a substantially U-shape. The waste compartment 720 inter-locks with the working fluid compartment and has a portion above the working fluid compartment, a portion within the U-shape of the working fluid compartment, and a portion outside of and adjacent to the working fluid compartment. The working fluid compartment 710 and the waste compartment 720 are fluidically separate, and a septum connects between the compartment such that the working fluid compartment 710 and the waste compartment 720 are stationary relative to each other. The access opening 722 of the waste compartment 720 is adjacent to the top of the container, and the access opening 712 of the working fluid compartment 710 is adjacent to the bottom of the container.

Figure 8:
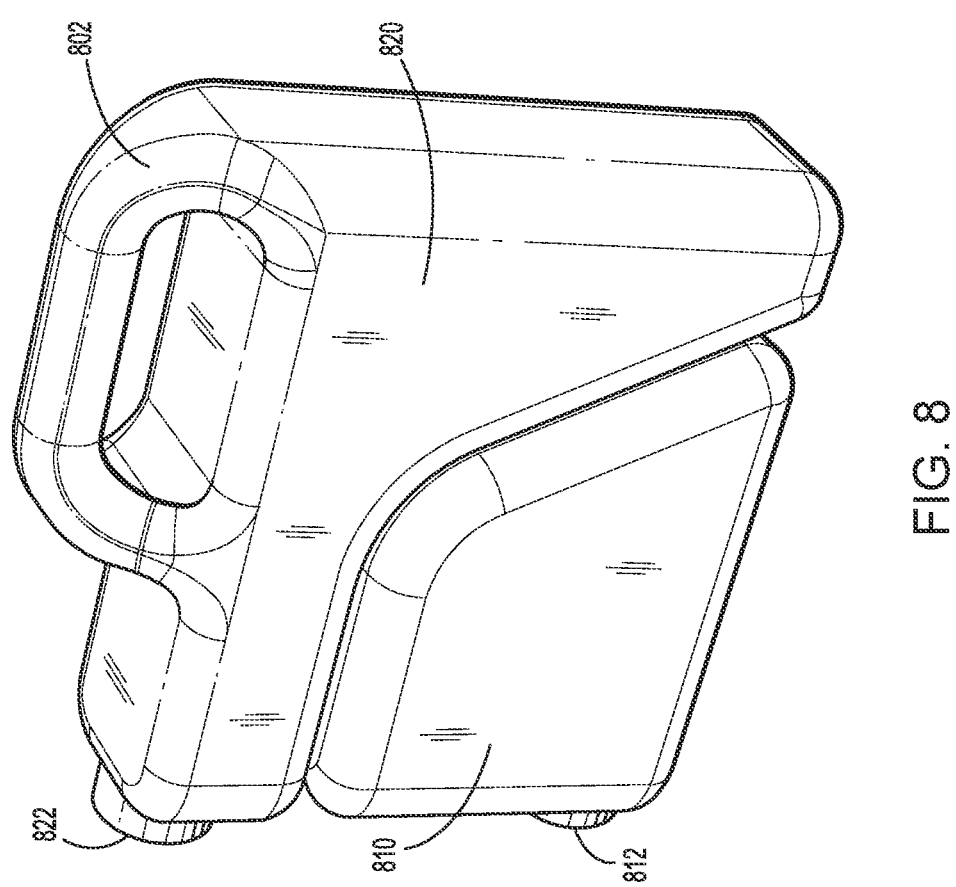
FIG. 8 is a diagram of yet another embodiment of a working fluid and waste container, in accordance with aspects of the present disclosure.

In the embodiment of FIG. 8, the working fluid and waste container includes a handle 802 at the top of the container. The handle 802 enables an operator to more easily carry the container when it is outside the medical diagnostic system. A handle 802 as shown in FIG. 8 can be applied to any other embodiment disclosed herein or any embodiment contemplated to be within the scope of the present disclosure. With continuing reference to FIG. 8, the working fluid compartment 810 is substantially in the shape of a trapezoid, and the waste compartment 820 has a complementary shape such that the overall shape of working fluid and waste container is square or rectangular, when not considering the shape of the handle 802. The working fluid compartment 810 and the waste compartment 820 are fluidically separate, and a septum connects between the compartment such that the working fluid compartment 810 and the waste compartment 820 are stationary relative to each other. The access opening 822 of the waste compartment 820 is adjacent to the top of the container, and the access opening 812 of the working fluid compartment 810 is adjacent to the bottom of the container.

Figure 9:
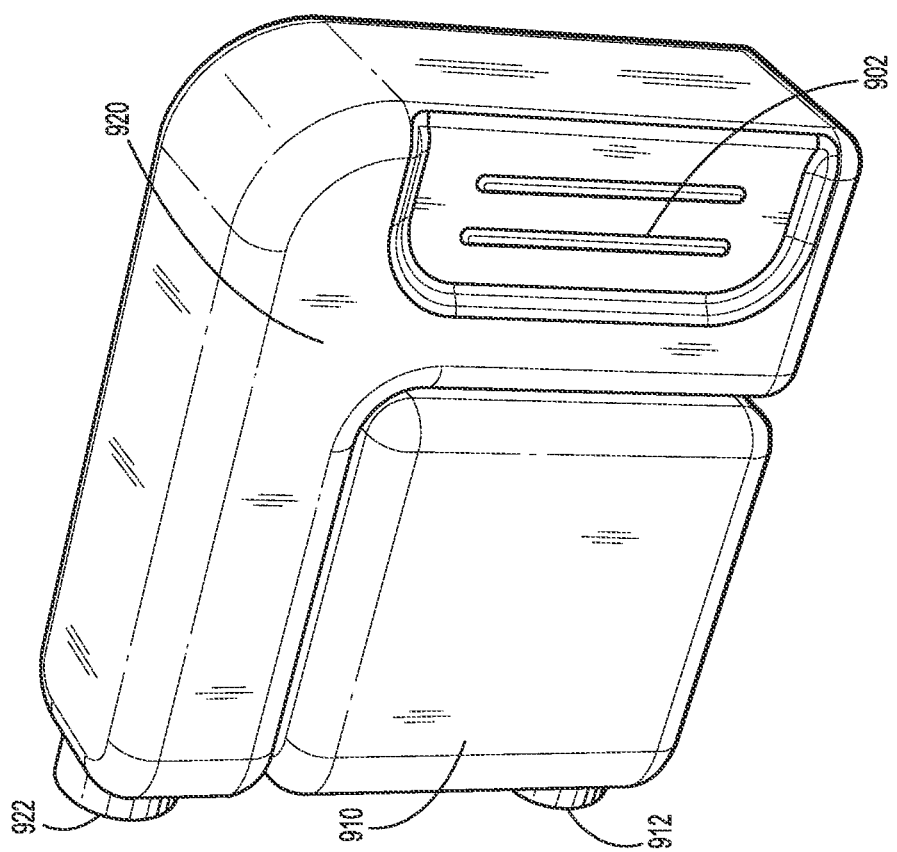
FIG. 9 is a diagram of still another embodiment of a working fluid and waste container, in accordance with aspects of the present disclosure.

In the embodiment of FIG. 9, the working fluid and waste container includes a grip-enhancement 902. The grip-enhancement 902 enables an operator to more easily handle the container when inserting the container into the medical diagnostics system or removing the container. A grip enhancement 902 as shown in FIG. 9 can be applied to any other embodiment disclosed herein or any embodiment contemplated to be within the scope of the present disclosure. With continuing reference to FIG. 9, the working fluid compartment 910 is substantially in the shape of a square, and the waste compartment 920 has a complementary shape such that the overall shape of working fluid and waste container is square or rectangular. The working fluid compartment 910 and the waste compartment 920 are fluidically separate, and a septum connects between the compartments such that the working fluid compartment 910 and the waste compartment 920 are stationary relative to each other. The access opening 922 of the waste compartment 920 is adjacent to the top of the container, and the access opening 912 of the working fluid compartment 910 is adjacent to the bottom of the container.

Figure 10:
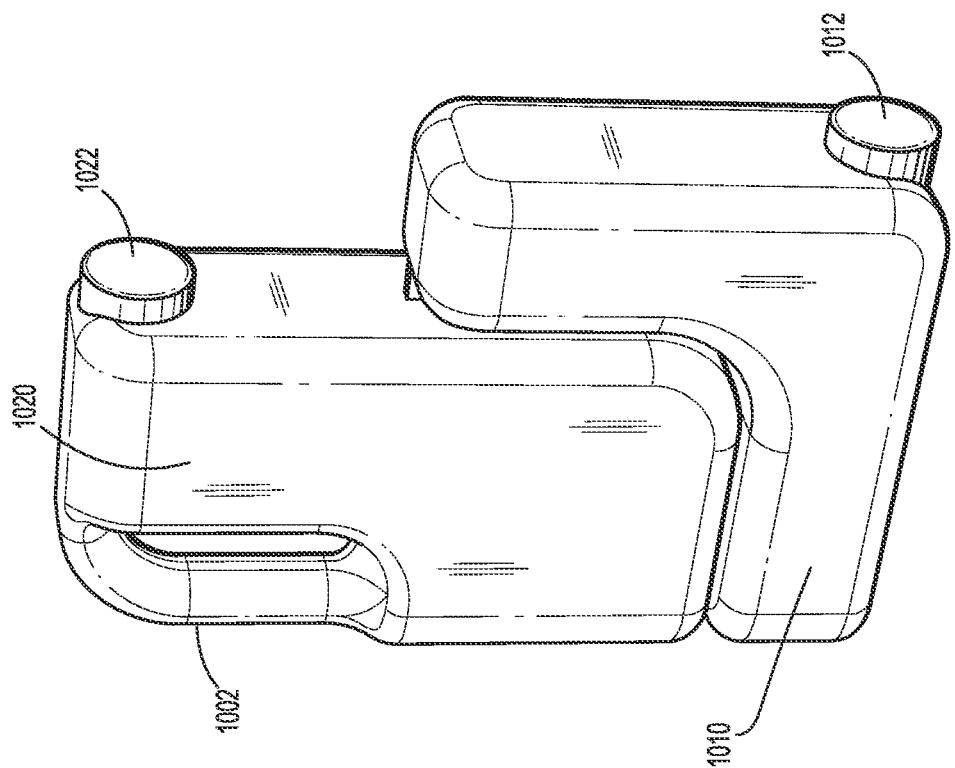
FIG. 10 is a diagram of another embodiment of a working fluid and waste container, in accordance with aspects of the present disclosure.

In the embodiment of FIG. 10, the working fluid and waste container includes a handle 1002 at a corner of the container. A handle 1002 as shown in FIG. 10 can be applied to any other embodiment disclosed herein or any embodiment contemplated to be within the scope of the present disclosure. With continuing reference to FIG. 10, the working fluid compartment 1010 has substantially an L-shape, and the waste compartment 1020 has a substantially rectangular shape, when not considering the shape of the handle 1002. The working fluid compartment 1010 and the waste compartment 1020 are fluidically separate, and a septum connects between the compartments such that the working fluid compartment 1010 and the waste compartment 1020 are stationary relative to each other. The access opening 1022 of the waste compartment 1020 is adjacent to the top of the container, and the access opening 1012 of the working fluid compartment 1010 is adjacent to the bottom of the container.

Figure 11:
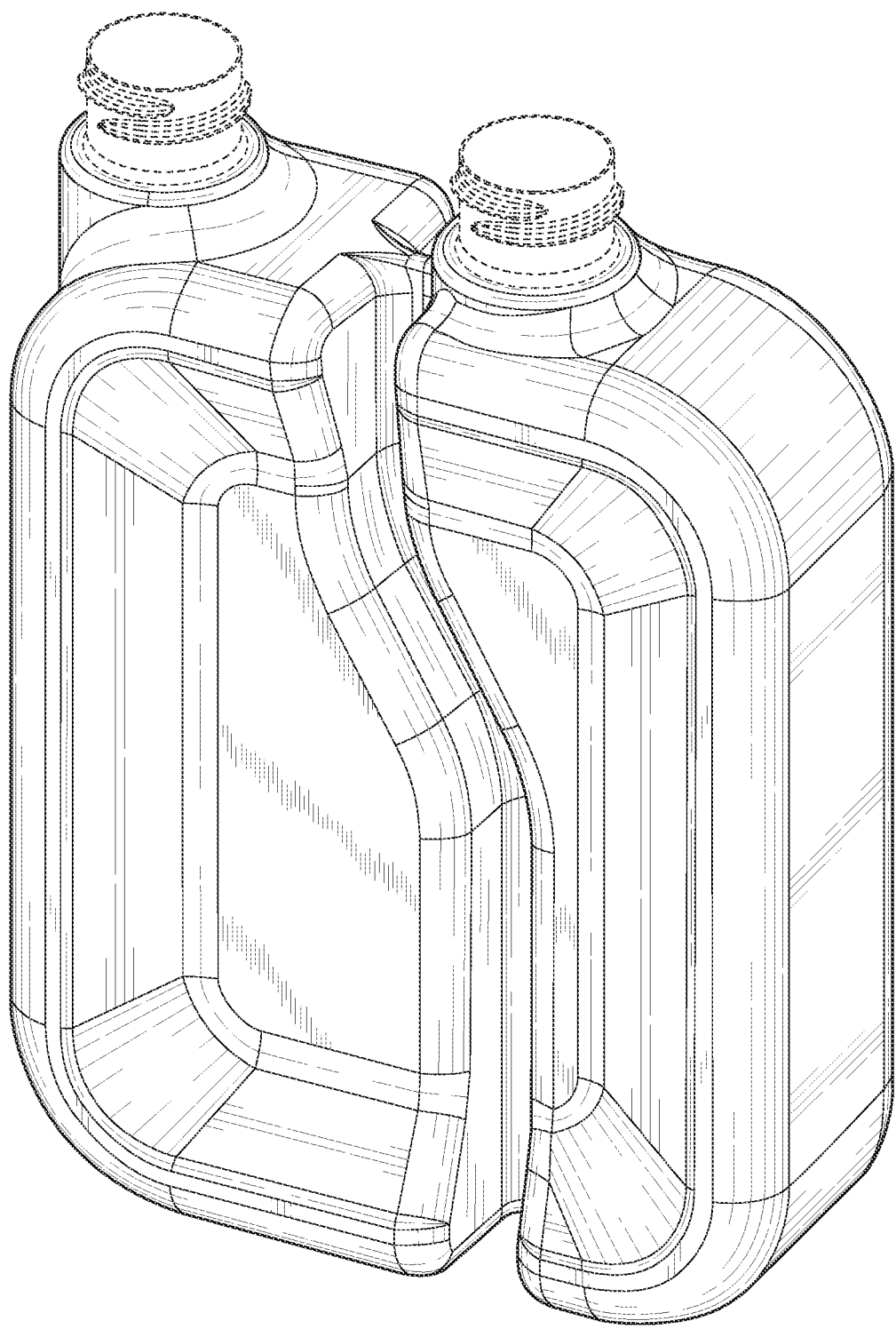
FIG. 11 is a perspective view of the reagent container of FIG. 2 with contour lines that more clearly show the shape of the container, in accordance with aspects of the present disclosure.
Figure 12:
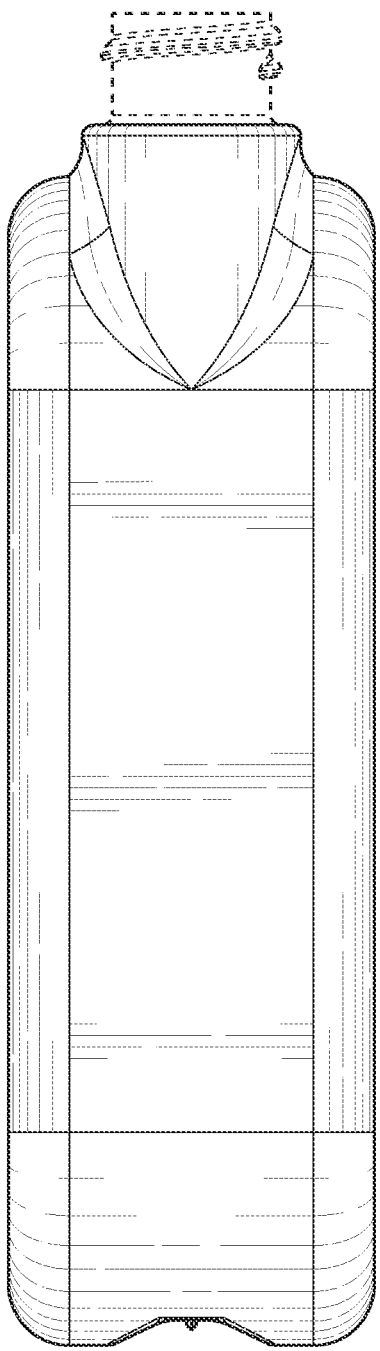
FIG. 12 is a bottom plan view of the reagent container of FIG. 2, in accordance with aspects of the present disclosure.
Figure 13:
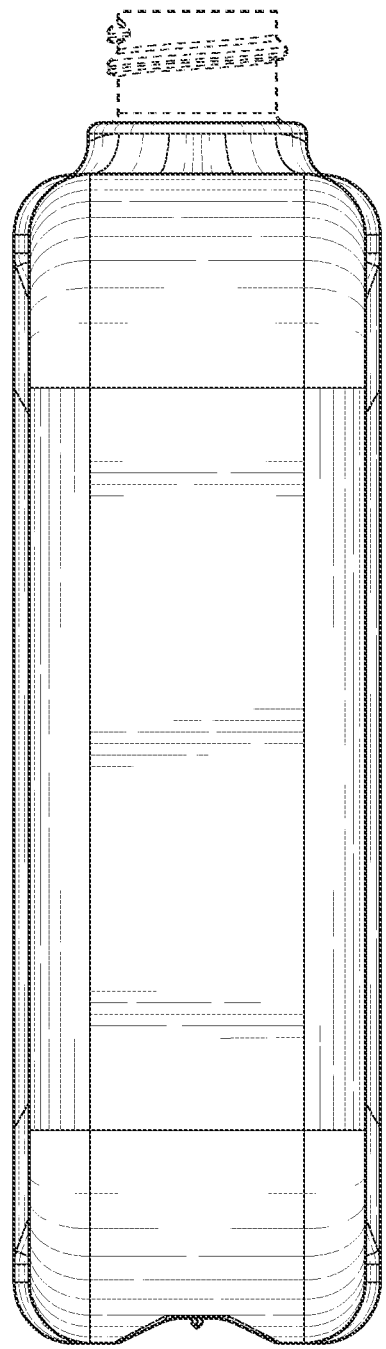
FIG. 13 is a top plan view of the reagent container of FIG. 2, in accordance with aspects of the present disclosure.
Figure 14:
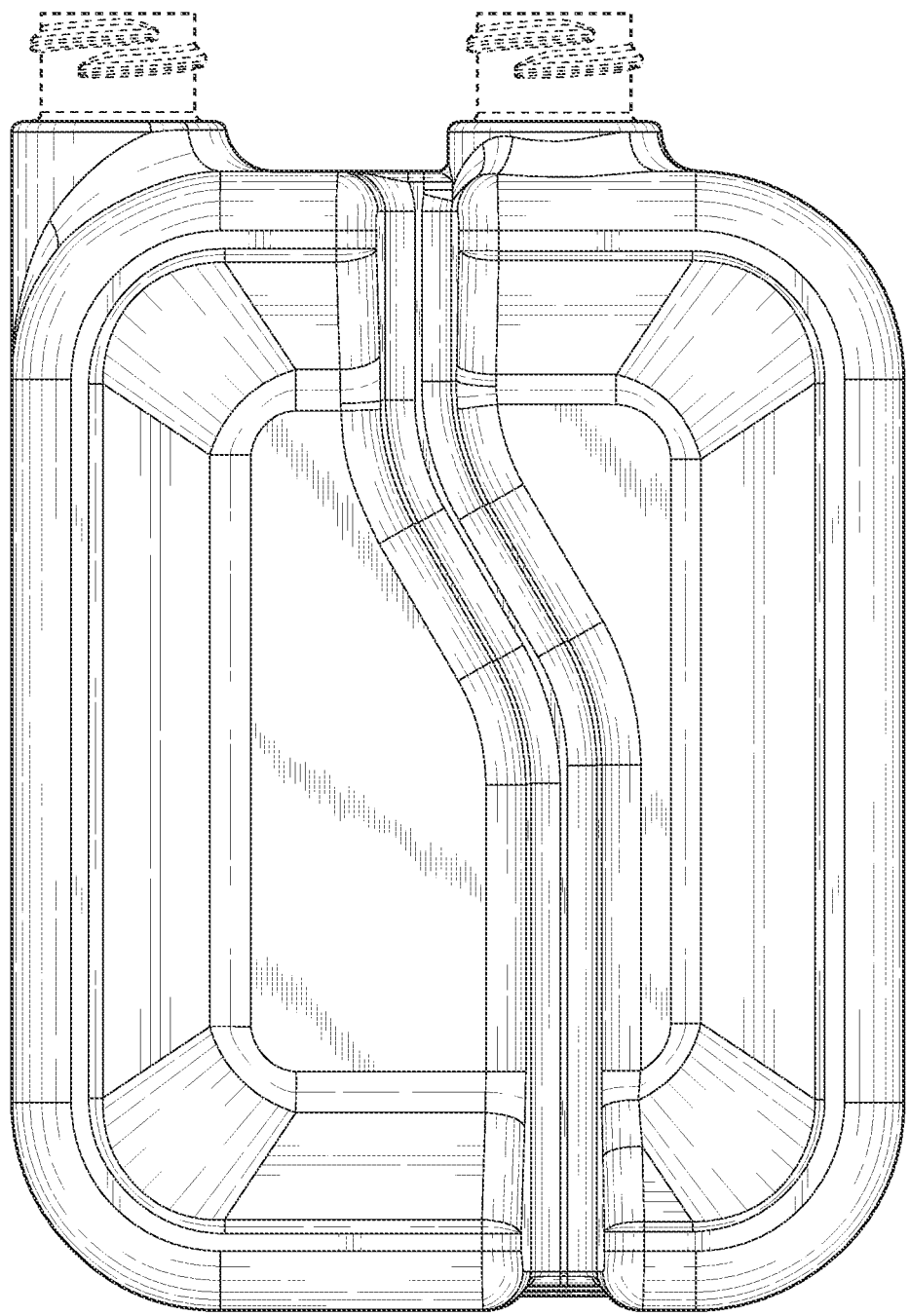
FIG. 14 is a left side elevational view of the reagent container of FIG. 2, in accordance with aspects of the present disclosure.
Figure 15:
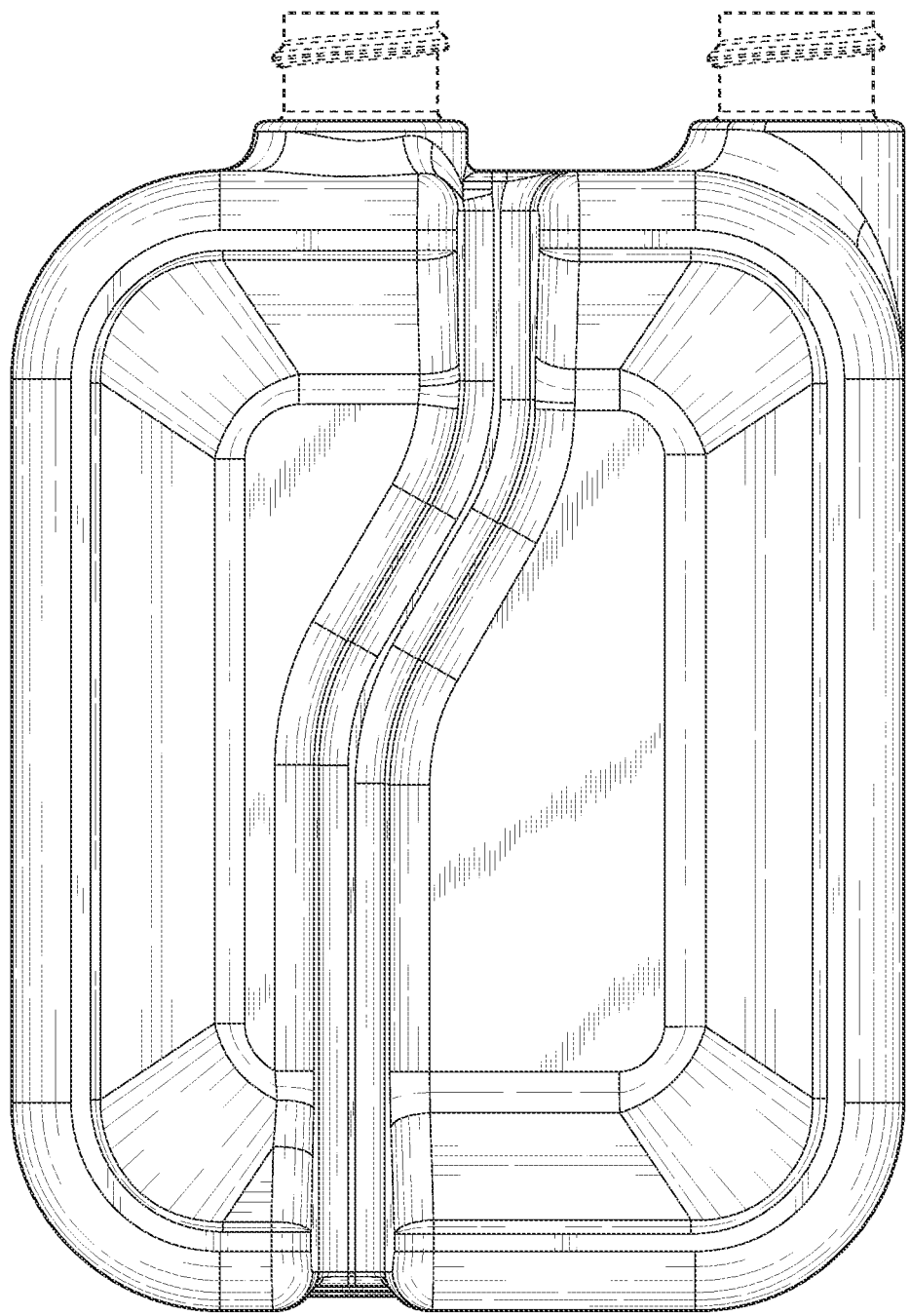
FIG. 15 is a right side elevational view of the reagent container of FIG. 2, in accordance with aspects of the present disclosure.
Figure 16:
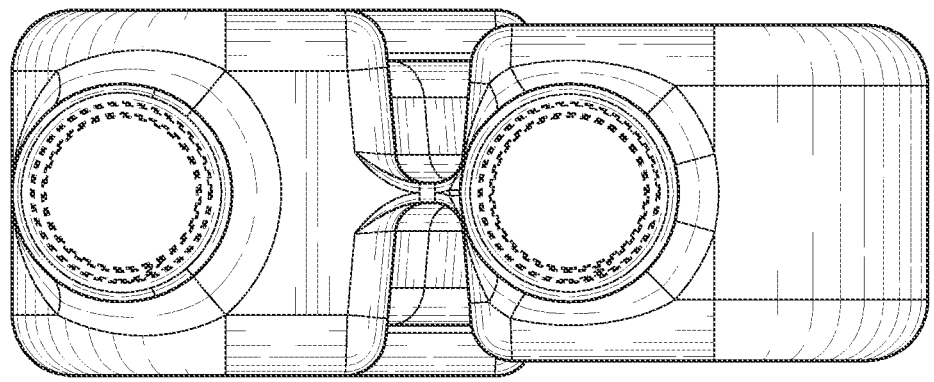
FIG. 16 is a front elevational view of the reagent container of FIG. 2, in accordance with aspects of the present disclosure.
Figure 17:
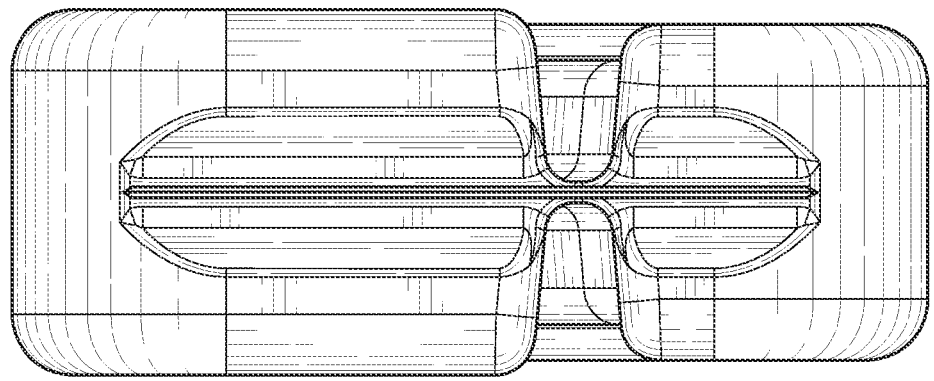
FIG. 17 is a rear elevational view of the reagent container of FIG. 2, in accordance with aspects of the present disclosure.
Figure 18:
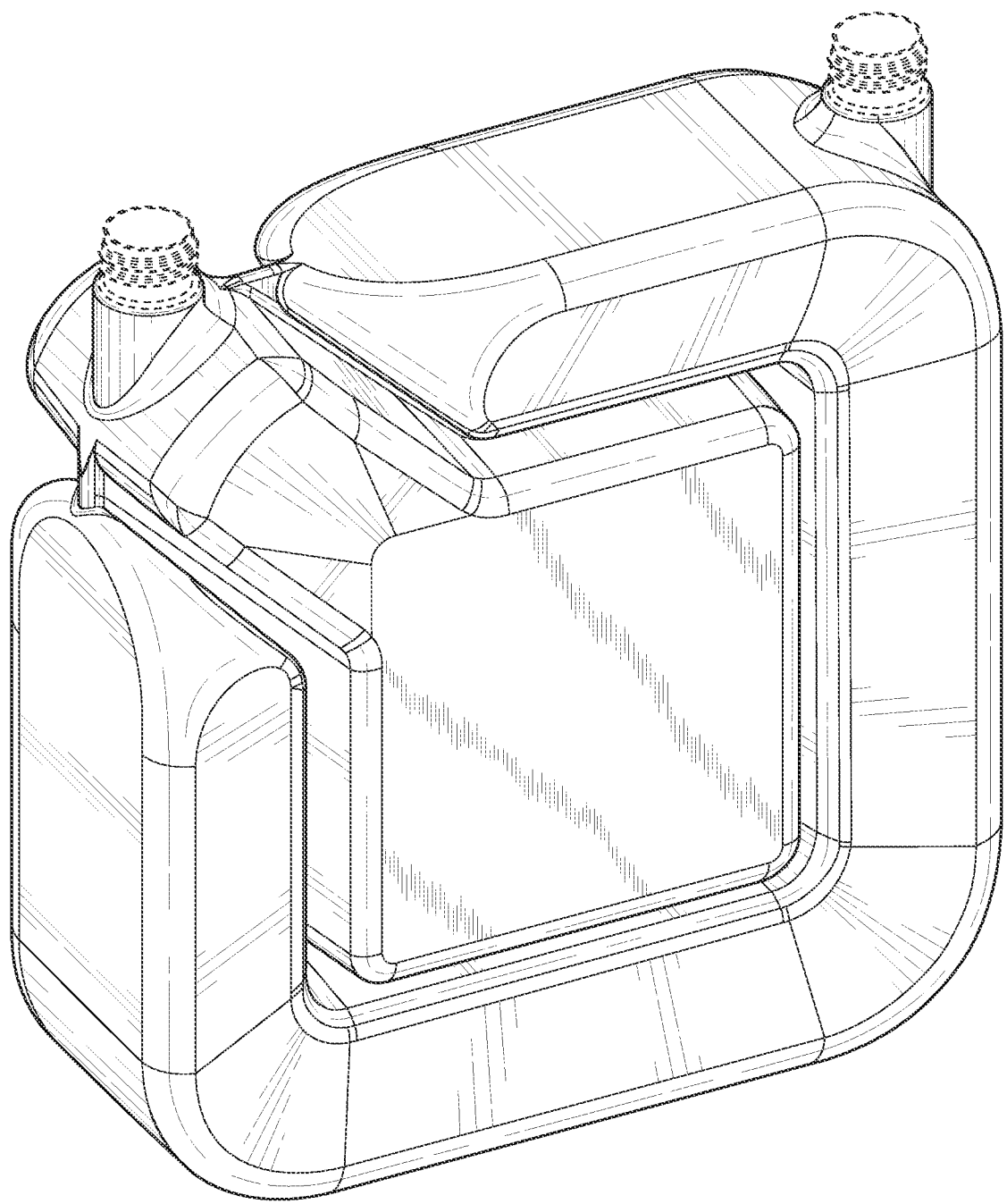
FIG. 18 is a perspective view of the working fluid and waste container of FIG. 5 with contour lines that more clearly show the shape of the container, in accordance with aspects of the present disclosure.
Figure 19:
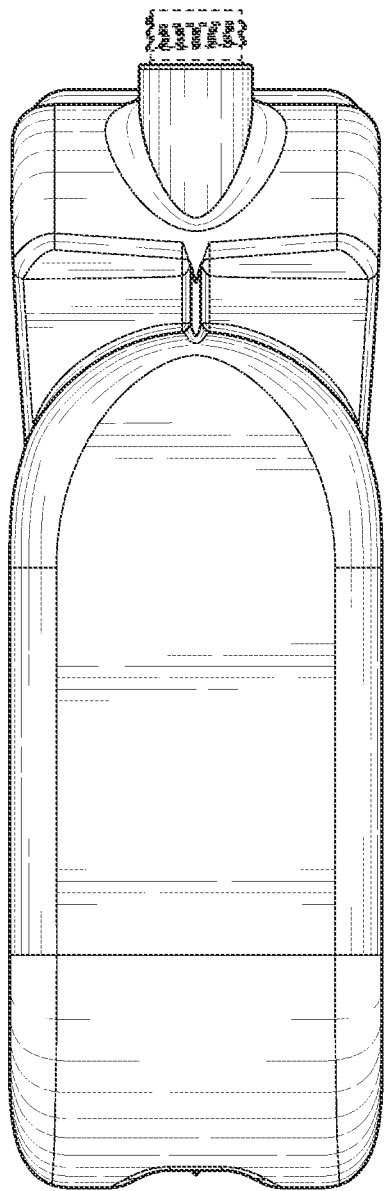
FIG. 19 is a bottom plan view of the working fluid and waste container of FIG. 5, in accordance with aspects of the present disclosure.
Figure 20:
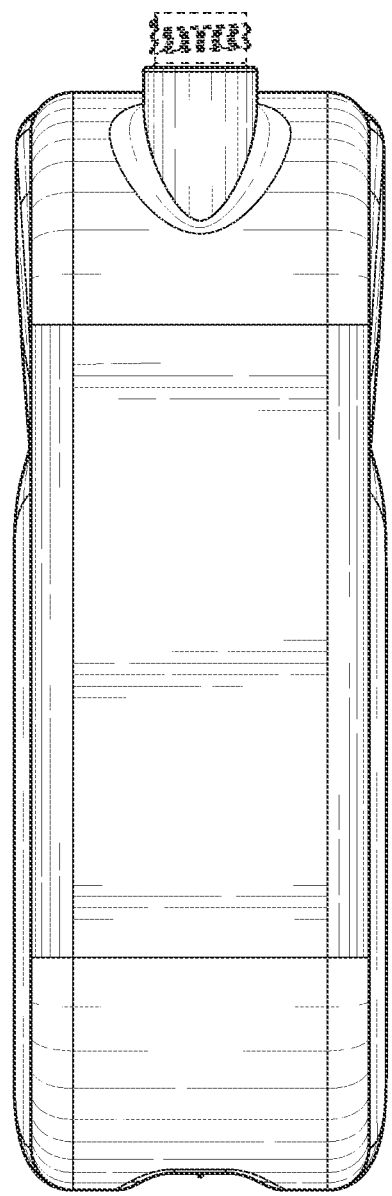
FIG. 20 is a top plan view of the working fluid and waste container of FIG. 5, in accordance with aspects of the present disclosure.
Figure 21:
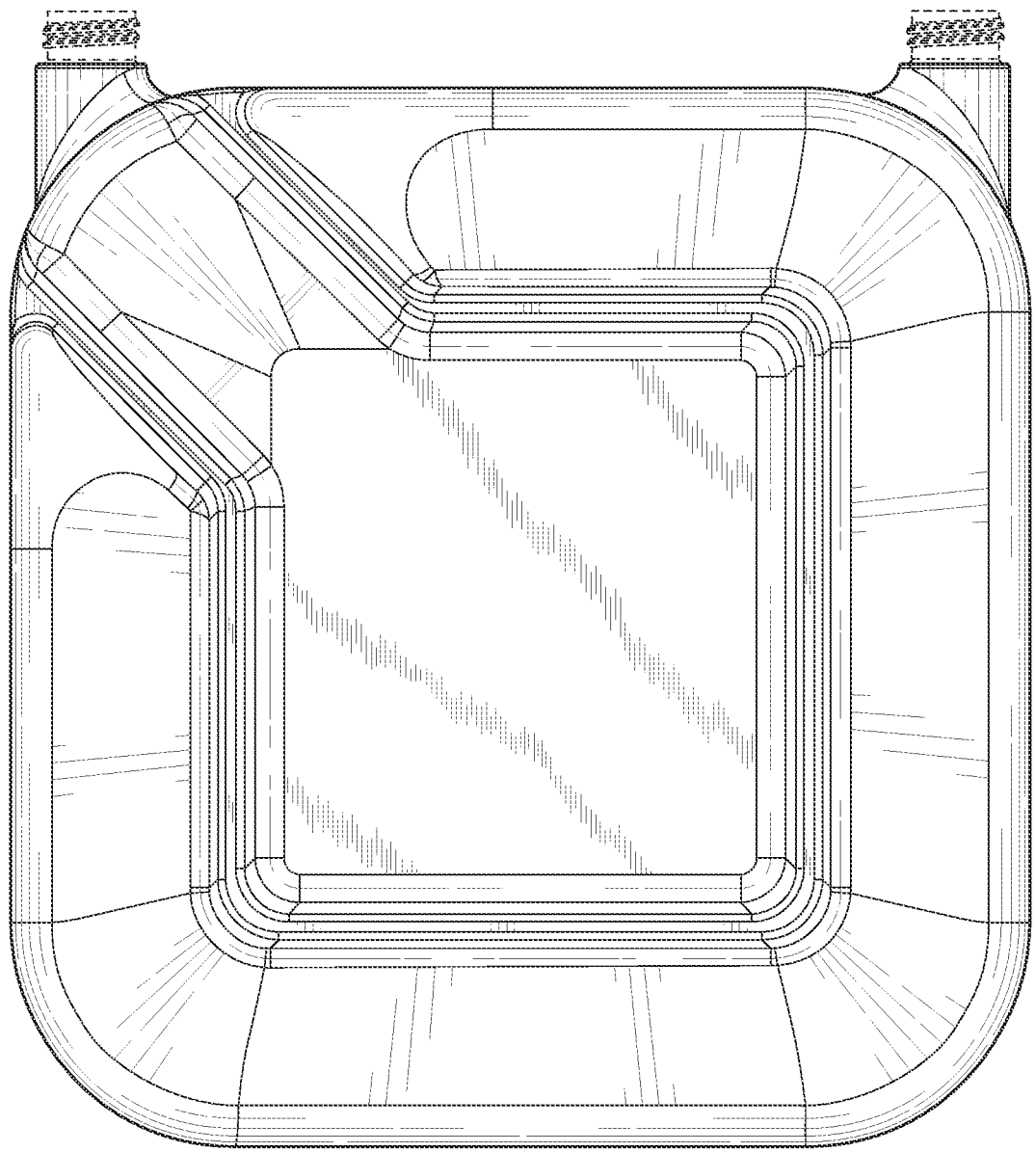
FIG. 21 is a left side elevational view of the working fluid and waste container of FIG. 5, in accordance with aspects of the present disclosure.
Figure 22:
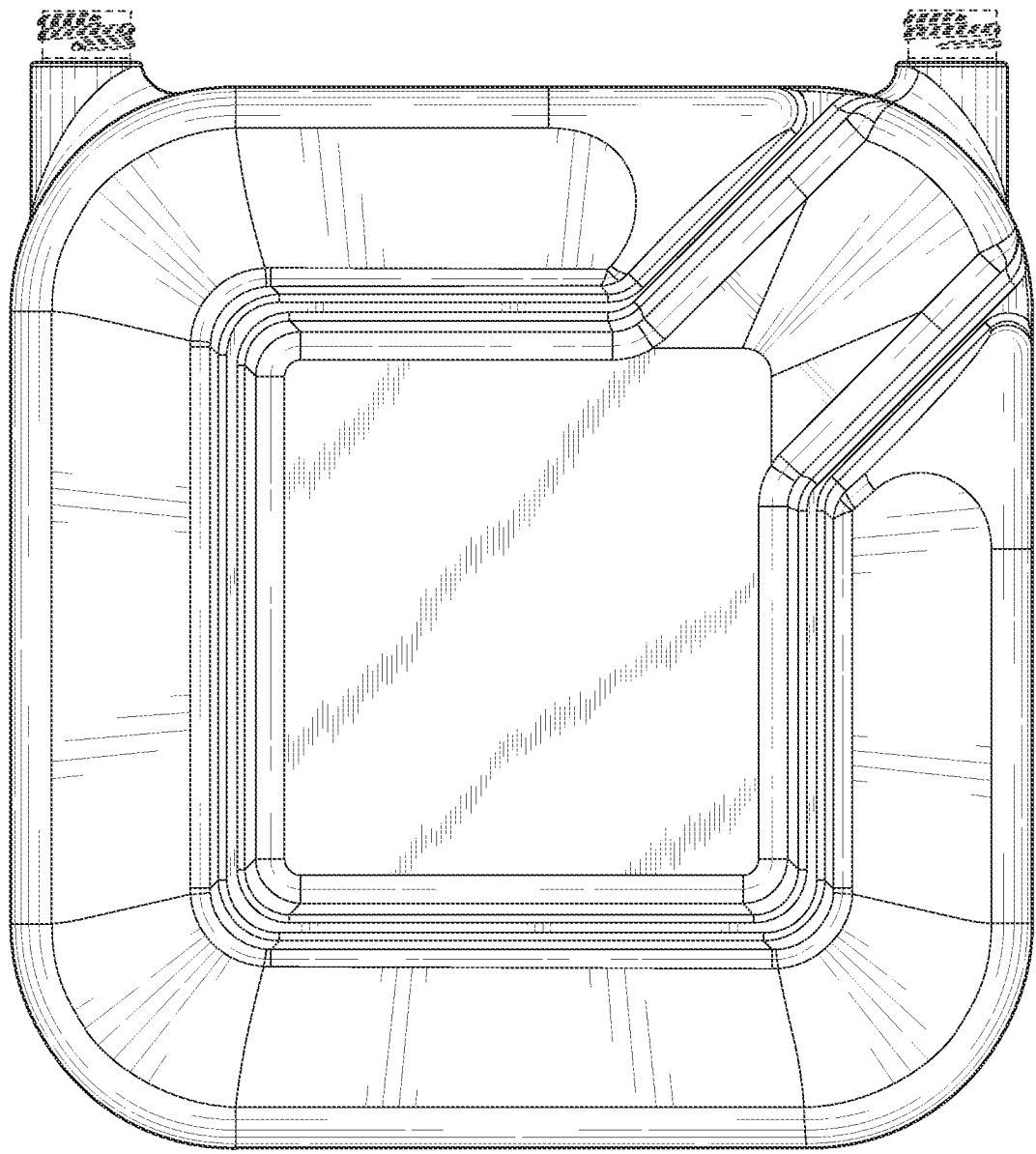
FIG. 22 is a right side elevational view of the working fluid and waste container of FIG. 5, in accordance with aspects of the present disclosure.
Figure 23:
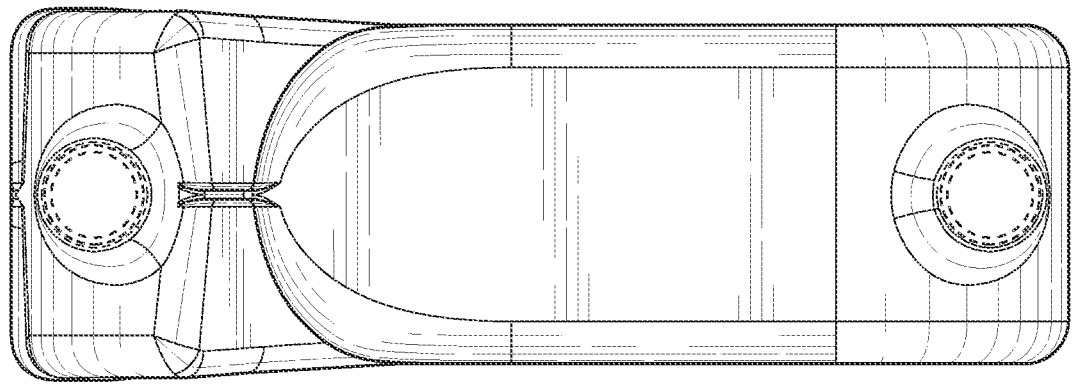
FIG. 23 is a front elevational view of the working fluid and waste container of FIG. 5, in accordance with aspects of the present disclosure.
Figure 24:
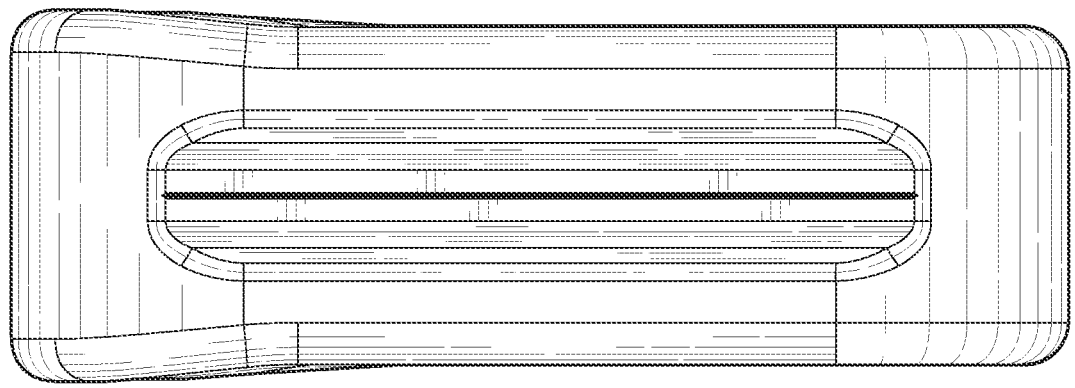
FIG. 24 is a rear elevational view of the working fluid and waste container of FIG. 5, in accordance with aspects of the present disclosure.

Accordingly, describe above are a medical diagnostic system and containers for the medical diagnostic system. FIGS. 11-17 show additional views of the reagent container of FIG. 2, with contour lines that more clearly illustrate the shape of the reagent container. In particular, FIG. 11 is a perspective view of the reagent container, FIG. 12 is a bottom plan view thereof, FIG. 13 is a top plan view thereof, FIG. 14 is a left side elevational view thereof, FIG. 15 is a right side elevational view thereof, FIG. 16 is a front elevational view thereof, and FIG. 17 is a rear elevational view thereof. As shown in FIGS. 11-17, the perimeter of the illustrated reagent container is wider than the rest of the reagent container and permits an operator to more readily grasp the reagent container along any portion of the perimeter. FIGS. 18-24 show additional views of the working fluid and waste container of FIG. 5, with contour lines that more clearly illustrate the shape of the working fluid and waste container. In particular, FIG. 18 is a perspective view of the working fluid and waste container, FIG. 19 is a bottom plan view thereof, FIG. 20 is a top plan view thereof, FIG. 21 is a left side elevational view thereof, FIG. 22 is a right side elevational view thereof, FIG. 23 is a front elevational view thereof, and FIG. 24 is a rear elevational view thereof. As shown in FIGS. 18-24, the perimeter of the illustrated working fluid and waste container is wider than the rest of the container and permits an operator to more readily grasp the working fluid and waste container along any portion of the perimeter. The embodiments disclosed herein are merely exemplary and are not intended to limit the scope of the present disclosure.

The following describes a feature of present disclosure with reference to FIG. 1. In accordance with aspects of the present disclosure, the medical diagnostic system includes one or more cameras (not shown) for imaging encoded data-matrix codes on the reagent container 122 and the working fluid and waste container 132. The data-matrix codes on the containers 122, 132 can encode information such as expiration date, lot number, manufacturer identity, and authenticity, among other things. The camera can scan the data-matrix code to read this information, and the medical diagnostic system 100 can process and respond to the information in various ways.

In various embodiments, the larger receptacle 130 uses the camera (not shown) for imaging a data-matrix code on the working fluid and waste container 132, and the smaller receptacle 120 uses the same camera (not shown) for imaging a data-matrix code the reagent container 122. In various embodiments, the data-matrix codes are positioned on the containers 122, 132 such that the data-matrix codes can be read by the camera only when the containers 122, 132 are inserted into the medical diagnostic system 100 in a particular orientation.

Accordingly, various aspects and embodiments of the present disclosure are described above. The following will describe other aspects and embodiments of the present disclosure.

Figure 25:
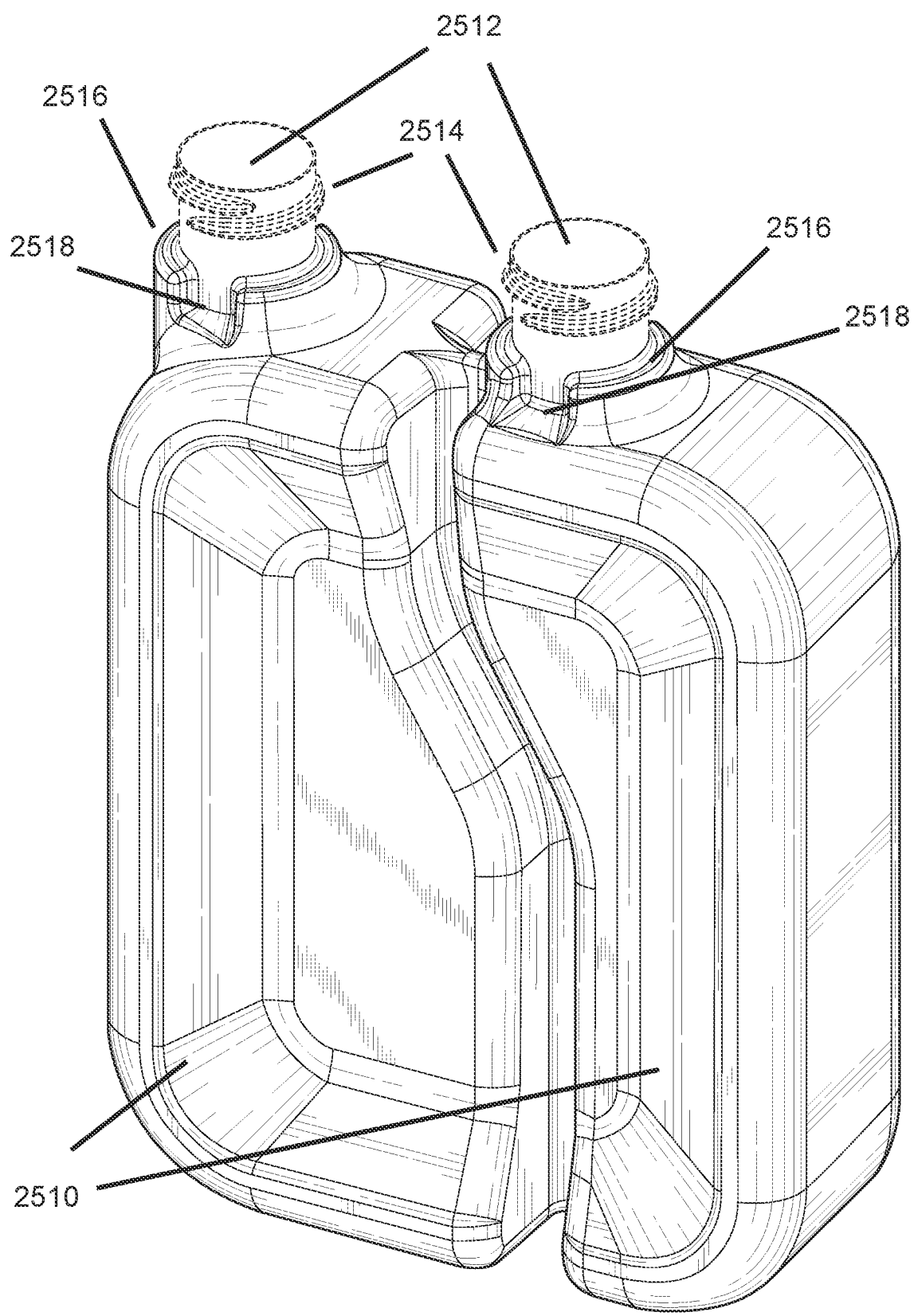
FIG. 25 is a perspective view of another embodiment of a reagent container with contour lines that more clearly show the shape of the container, in accordance with aspects of the present disclosure.

Referring to FIG. 25, there is shown an embodiment of a reagent container. Similar to the reagent container described in connection with FIG. 2 and FIG. 3, the reagent container of FIG. 25 includes two fluidically separate compartments 2510 that end with access openings 2512. The two compartments 2510 include reagents for use by the medical diagnostic system of FIG. 1. Each access opening 2512 is at the end of a neck 2514 that includes threads for receiving a cap (not shown). The neck 2514 is situated in a collar 2516 of the reagent container. In various embodiments, the neck 2514 and the collar 2516 are formed integrally in the same manufacturing process. In various embodiments, the neck 2514 and the collar 2516 are formed separately in separate molding processes and are then secured to each other.

In accordance with aspects of the present disclosure, each collar 2516 includes one or more notches for receiving a container engagement mechanism, which will be described in connection with FIGS. 27-33. In the illustrated embodiment, one notch 2518 can be seen for each collar 2516. In various embodiments, the other side of the collar 2516 may or may not include another notch or other notches. In various embodiments, each collar 2516 can include multiple notches, such as two or more notches, which can be arranged or positioned at various regions of the collar 2516. In various embodiments, different collars may have the same number of notches or different numbers of notches. In various embodiments, the notch or notches may have different shapes or dimensions than as illustrated.

Figure 26:
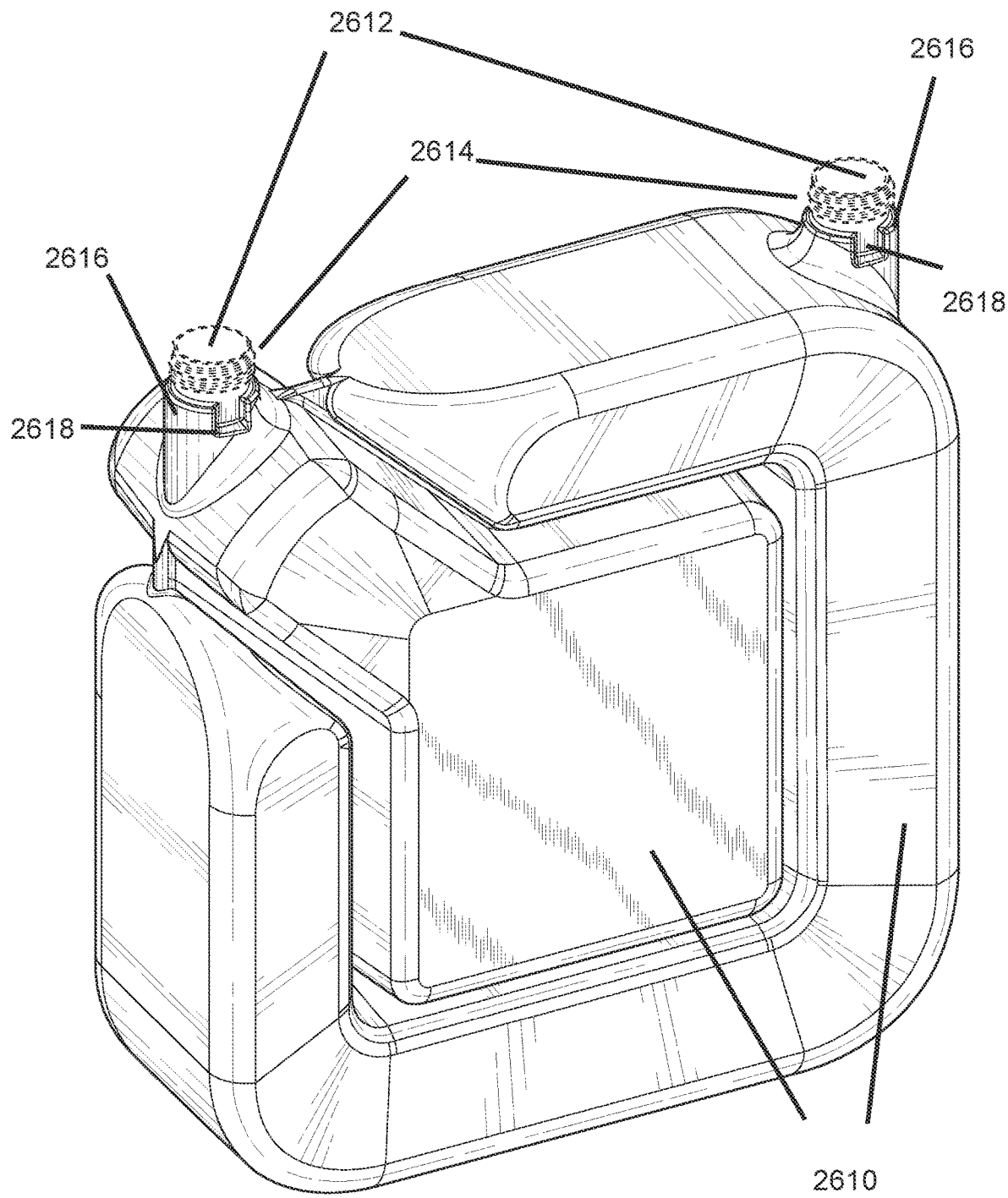
FIG. 26 is a perspective view of another embodiment of a working fluid and waste container with contour lines that more clearly show the shape of the container, in accordance with aspects of the present disclosure.

FIG. 26 is shows an embodiment of a working fluid and waste container. Similar to the working fluid and waste container described in connection with FIG. 5 and FIG. 6, the working fluid and waste container of FIG. 26 includes a working fluid compartment that is fluidically separate from a waste compartment. Each compartment 2610 ends in an access opening 2612, and each access opening 2612 is at the end of a neck 2614 that includes threads for receiving a cap (not shown). The neck 2614 is secured to a collar 2616, which can have one or more notches 2618 for receiving a container engagement mechanism. The embodiments and variations of the notches described in connection with FIG. 25 also apply to the collar of FIG. 26.

Figure 27:
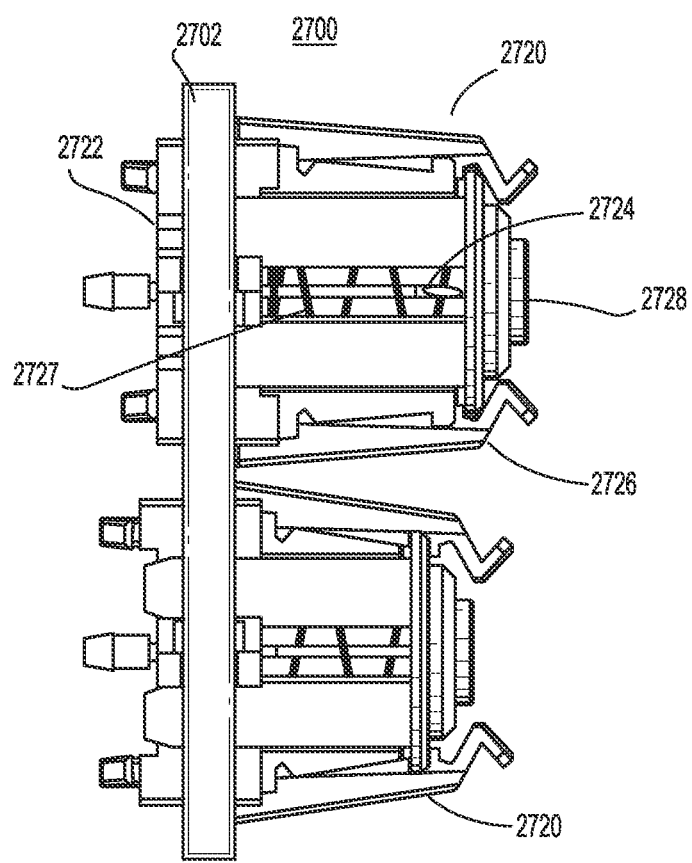
FIG. 27 is a diagram of an embodiment of a container engagement mechanism having two compartment engagement mechanisms, in accordance with aspects of the present disclosure.

Referring now to FIG. 27, there is shown a diagram of an embodiment of a container engagement mechanism 2700. The illustrated container engagement mechanism 2700 includes two compartment engagement mechanisms 2720.

With reference also to FIG. 1, the container engagement mechanism 2700 can be positioned within the receptacles 120, 130 of the medical diagnostic system 100 described in connection with FIG. 1, such as positioned at the back walls 2702 of the receptacles 120, 130.

In the illustrated embodiment, each compartment engagement mechanism 2720 includes a hub 2722, a needle 2724, two or more engagement arms 2726, a spring 2727, and a needle cover 2728. The hub 2722 is secured to and through a wall 2702 of the receptacle, such as the back wall of the receptacle. The hub 2722 holds and secures the needle 2724, the engagement arms 2726, and the needle cover 2728. In various embodiments, the needle 2724 can be held to be perpendicular to or substantially perpendicular to the wall 2702 of the receptacle. In various embodiments, the needle 2724 can be firmly held by the hub 2722 such that the needle 2724 does not dislodge from the hub 2722 when it accesses a compartment of a container.

In accordance with aspects of the present disclosure, the hub 2722 holds the needle cover 2728 and serves as a guide to permit the needle cover 2728 to slide through or along the hub 2722. The structure of the hub 2722 and the needle cover 2728 will be described in more detail in connection with FIGS. 28-30. For the purpose of FIG. 27, it is noted that the needle cover 2728 can slide through or along the hub 2722 in a direction that is parallel to the direction of the needle 2724 and/or that is perpendicular to the wall 2702 of the receptacle. The spring 2727 is positioned between the needle cover 2728 and the hub 2722 in a manner that biases the needle cover 2728 in a covered position that covers the needle 2724.

The hub 2722 also holds the engagement arms 2726 such that the engagement arms 2726 secure the needle cover 2728 when the needle cover 2728 is in the covered position. The engagement arms 2726 are secured to the hub 2722 in a manner such that the engagement arms 2726 do not move through the hub 2722. However, at least a portion of each engagement arm 2726 is semi-flexible so that each engagement arm can flex radially away from the needle 2724 and the needle cover 2728. In various embodiments, a compartment engagement mechanism 2720 can include one engagement arm 2726. In various embodiments, a compartment engagement mechanism 2720 can include more than one engagement arm 2726. In various embodiments, the engagement arm(s) 2726 can be arranged or positioned in various ways different from the arrangement illustrated in FIG. 27.

Figure 28:
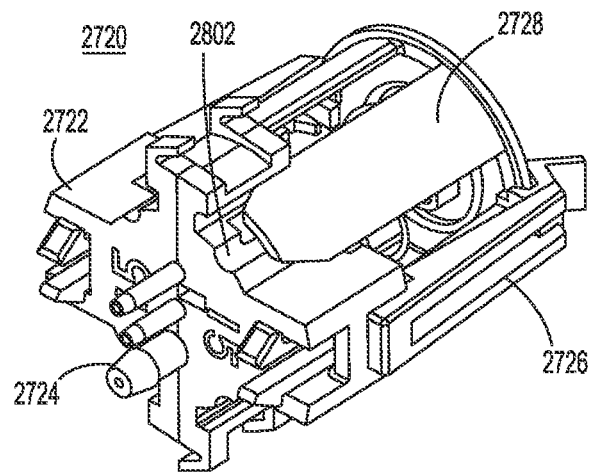
FIG. 28 is a perspective view of the compartment engagement mechanism of FIG. 27, in accordance with aspects of the present disclosure.

FIG. 28 shows a perspective view of the compartment engagement mechanism 2720 of FIG. 27 without the wall of the receptacle, including the hub 2722, the needle cover 2728, two engagement arms 2726, and three needles 2724. Although the illustrated embodiment includes three needles 2724, another number of needles can be used in various embodiments, such as fewer than three needles or more than three needles. Additionally, the needles 2724 are arranged in a line in FIG. 28. In various embodiments, multiple needles can be arranged in another manner, such as in a triangle or in another shape or another arrangement. As shown in FIG. 28, the hub 2722 includes guide slots 2802 which receive a portion of the needle cover 2728 and permit the portion of the needle cover 2728 to slide through or along the hub 2722.

Figure 29:
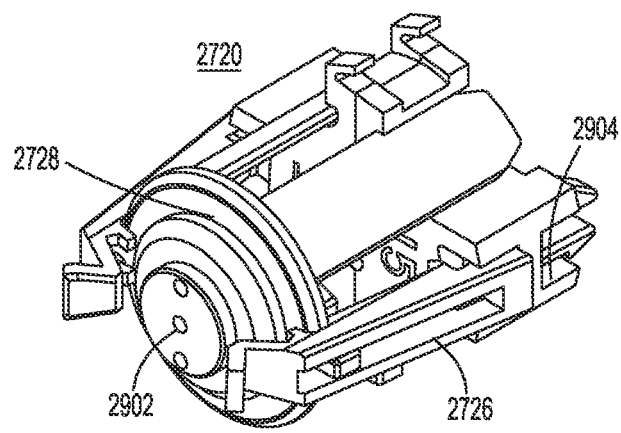
FIG. 29 is another perspective view of the compartment engagement mechanism of FIG. 27, in accordance with aspects of the present disclosure.

FIG. 29 shows another perspective view of the compartment engagement mechanism 2720, including a container-facing end of the mechanism. As shown in FIG. 29, the container-facing end of the needle cover 2728 includes apertures 2902. The apertures 2902 are aligned with the needles 2724 such that the needles 2724 extend through the apertures 2902 when the needle cover 2728 slides through or along the hub 2722. The hub 2722 also includes slots 2904 that receive and secure the engagement arms 2726. In various embodiments, when the engagement arms 2726 are secured to the hub 2722, the engagement arms 2726 will no longer slide through the hub 2722. FIGS. 28 and 29 are exemplary, and variations of or other embodiments of a compartment engagement mechanism are contemplated to be within the scope of the present disclosure.

FIG. 30 is a diagram of certain components of the container engagement mechanism 2700 of FIGS. 27-29, including an engagement arm 2726, a needle cover 2728, and a hub 2722. In the illustrated embodiment, the hub 2722 is formed from two identical half-components which combine to form the hub 2722 illustrated in FIGS. 27-29. In various embodiments, the hub 2722 may be formed as one unitary component. In various embodiments, the hub 2722 can be made from a plastic material.

In the illustrated embodiment, the needle cover 2728 includes a cap 3002 and glide posts 3004 attached to the cap 3002. In various embodiments, the cap 3002 and the glide posts 3004 can have various shapes, including shapes different from those illustrated in FIG. 30. In various embodiments, the number of glide posts 3004 can vary, including fewer than four glide posts or more than four glide posts. The hub 2722 can include a corresponding number of guide slots 3012 to receive the glide posts 3004 of the needle cover 2728. In various embodiments, the needle cover 2728 can be made from a plastic material.

The engagement arm 2726 includes a base portion 3022, an elbow portion 3024, and a grasping portion 3026. The base portion 3022 is configured to sit within the hub 2722 and remain secured to the hub 2722 by ledges that are positioned to abut the hub 2722. The hub 2722 includes a slot 3014 that receives the base portion 3022 of the engagement arm 2726. The elbow portion 3024 of the engagement arm 2726 is connected to the base portion 3022, and the grasping portion 3026 of the engagement arm 2726 is connected to the elbow portion 3024. The elbow portion 3024 is semi-flexible so as to flex and permit the grasping portion 3026 to move radially closer to or farther away from the needle cover of the compartment engagement assembly. The end of the grasping portion 3026 includes a wedge shape pointed towards the needle cover of the compartment engagement assembly. In various embodiments, the engagement arm 2726 can be made from a plastic material.

Figure 31:
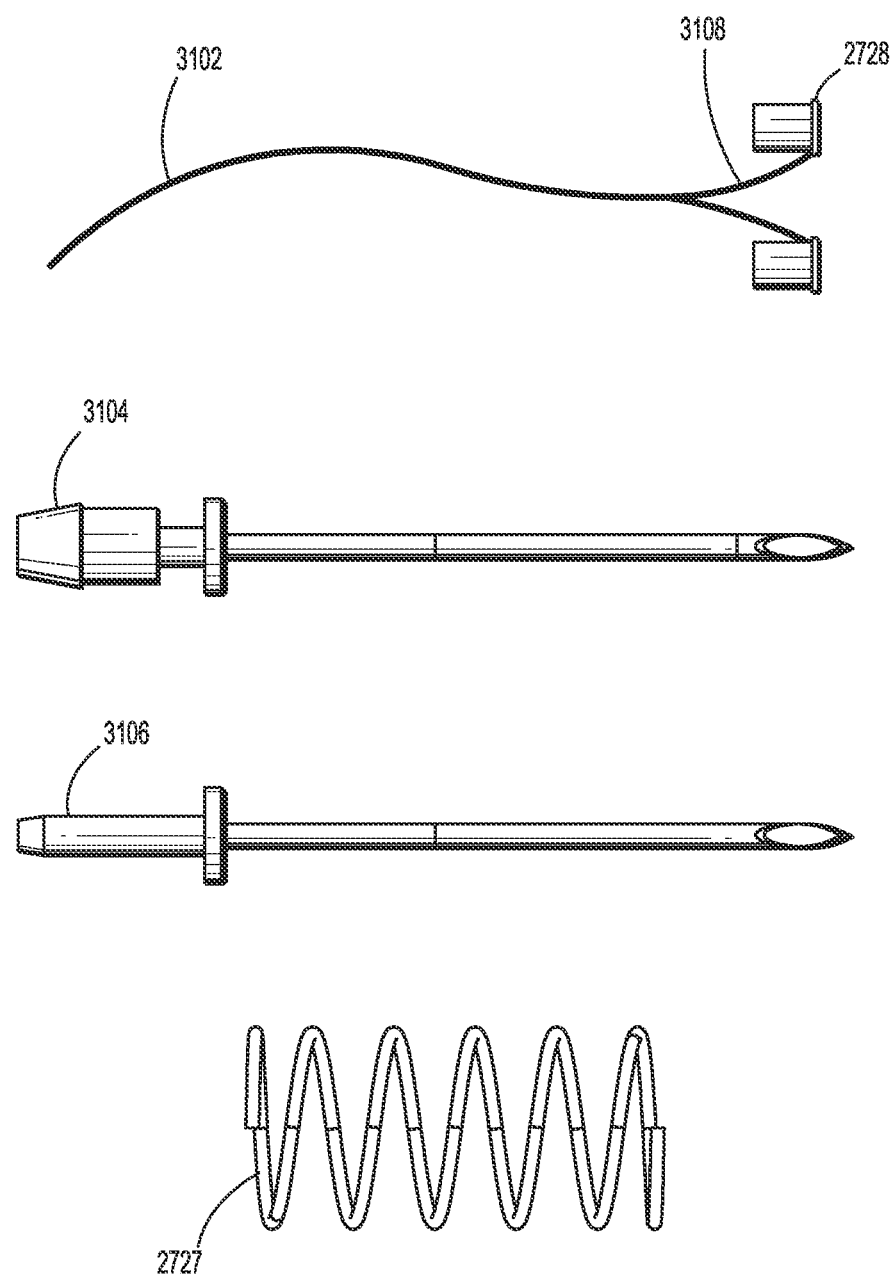
FIG. 31 is a diagram of certain other components of the compartment engagement mechanism of FIG. 27, in accordance with aspects of the present disclosure.

FIG. 31 is a diagram of certain other components of the compartment engagement mechanism 2720, including a level detection mechanism 3102, a coated needle 3104, an uncoated needle 3106, and a spring 2727. The spring 2727, as described above, can be positioned to bias the needle cover 2728 in a covered position that covers the needle(s). In various embodiments, the coated needle 3104 can be coated with a material that has lower friction and that allows the needle 3104 to access a compartment more smoothly. In various embodiments, one or more uncoated needle 3106 may accompany a coated needle to provide greater flow to or from a container. In various embodiments, the needles are sharp and strong enough to puncture a cap of a container.

The level detection mechanism 3102 includes a cable having a detection end and a container end. At the container end, the cable is split into a number of leads 3108 that corresponds to the number of access openings of the container. The containers described above herein include two access openings. Therefore, the illustrated level detection mechanism 3102 splits into two leads 3108 at the container end. Each lead 3108 is connected to a needle cover. When both needle covers move at the same speed, tension remains on both leads 3108 and the detection end of the cable remains level. When one needle cover moves faster than the other needle cover, one lead loses tension and the detection end of the cable becomes non-level. Thus, if a container is tilted when it is inserted to the container engagement mechanism, the level detection mechanism 3102 will detect the tilt, and the medical diagnostic system can inform the user accordingly. The level detection mechanism described above is exemplary, and other level detection mechanisms are contemplated to be within the scope of the present disclosure.

Figure 32:
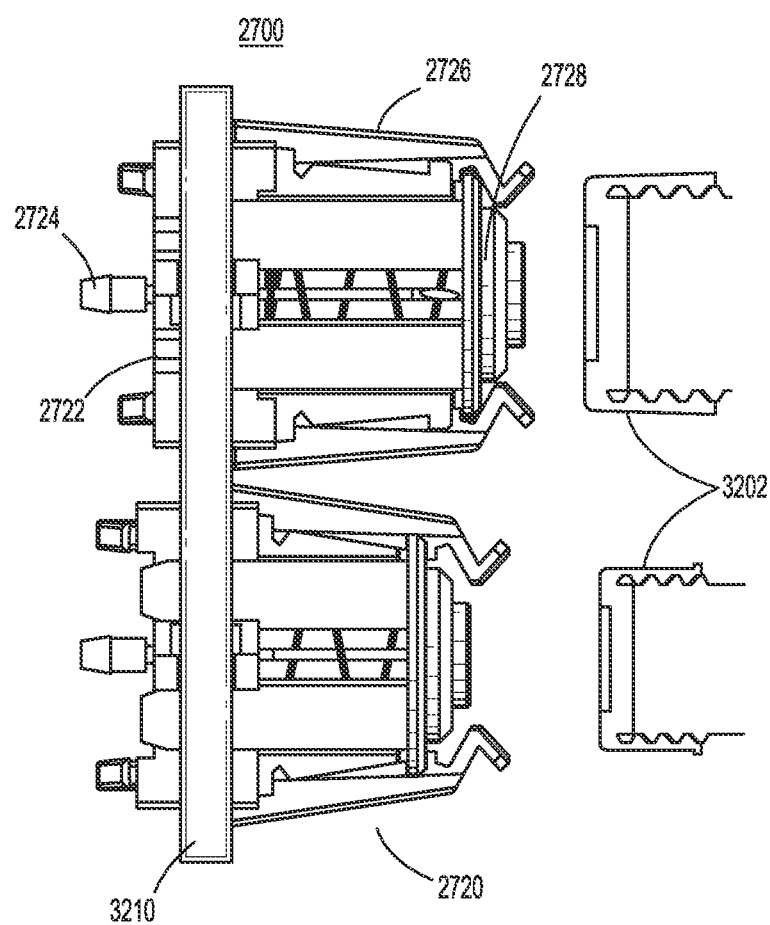
FIG. 32 is a diagram of the container engagement mechanism of FIG. 27 before engaging a container, in accordance with aspects of the present disclosure.
Figure 33:
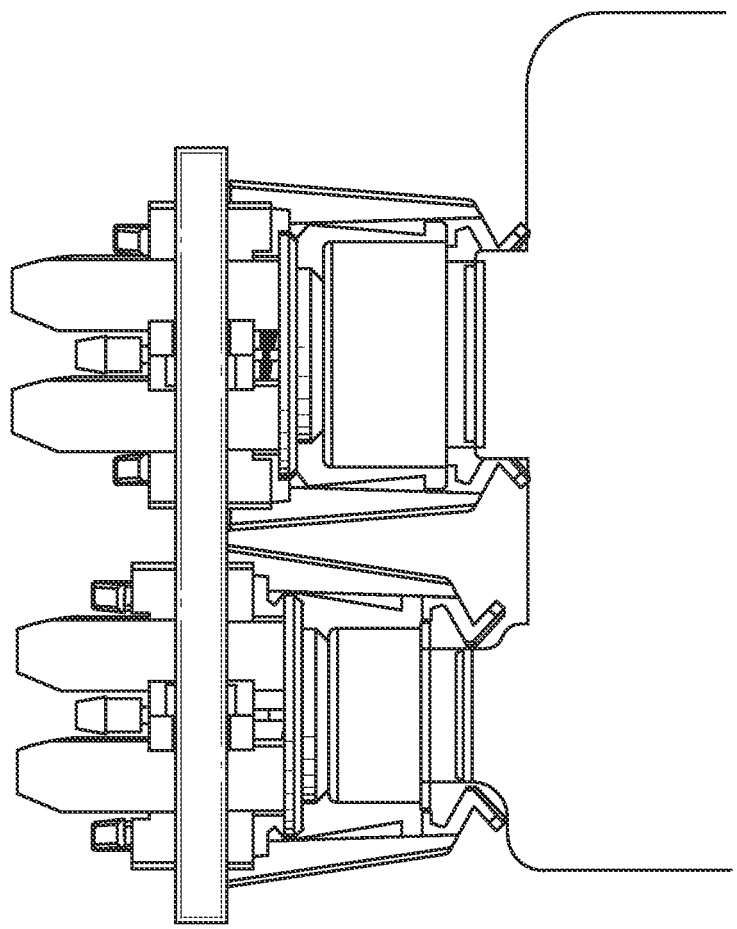
FIG. 33 is a diagram of the container engagement mechanism of FIG. 27 after engaging a container, in accordance with aspects of the present disclosure.

FIG. 32 is a diagram of the container engagement mechanism 2700 before engaging the caps 3202 of a container. The container can be a reagent container or a working fluid and waste container. In the case of a working fluid and waste container, the two compartment engagement mechanisms 2720 may be separated more than as illustrated. The caps 3202 and the compartment engagement mechanisms 2720 are sized dimensionally to couple with each other. For example, the cap 3202 is sized to contact the wedge-shaped ends of the engagement arms 2726 and to cause the engagement arms 2726 to flex away from the needle cover 2728 and release the needle cover 2728. Once the needle cover 2728 is no longer grasped by the engagement arms 2726, the cap 3202 can press against the needle cover 2728 and cause it to slide through or along the hub 2722 and expose the needles 2724. The needles 2724 puncture the cap 3202 to access the compartment of the container. When the container is fully engaged with the container engagement mechanism 2720, the engagement arms 2726 are received by the notches in the collar of the container, as described above in connection with FIGS. 27 and 28, and as shown in FIG. 33. In various embodiments, the grasping portion of the engagement arms 2726 can grasp the cap 3202 to secure the container within the receptacle, as shown in FIG. 33.

Referring again to FIG. 32, and in accordance with aspects of the present disclosure, one compartment engagement mechanism may be smaller than the other compartment engagement mechanism, such that the container-facing ends of the two compartment engagement mechanisms may not be the same distance from the wall 3210 of the receptacle. Additionally, the caps 3202 of the container may also be different sizes and may extend a different distance from the body of the container. Variations in the sizes and arrangements of the compartment engagement mechanisms 2720 and of the caps 3202 of a container are contemplated to be within the scope of the present disclosure.

Figure 34:
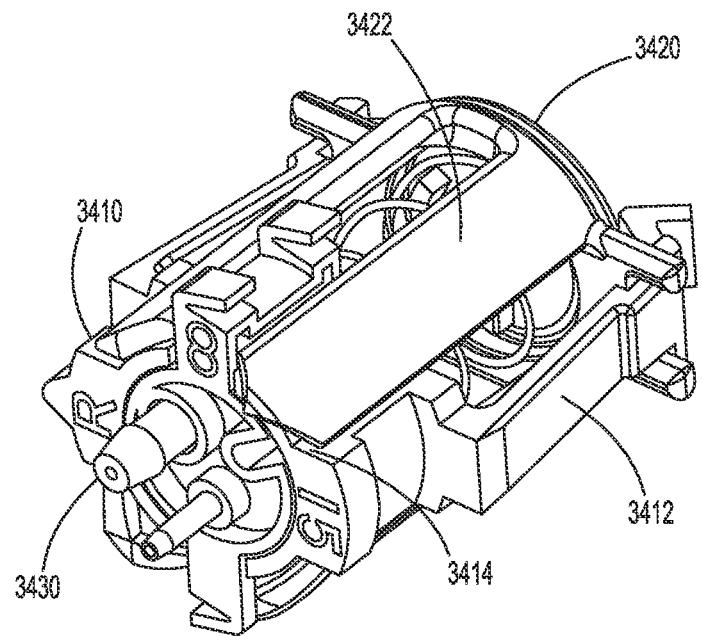
FIG. 34 is a perspective view of another embodiment of a compartment engagement mechanism, in accordance with aspects of the present disclosure.

FIG. 34 shows a perspective view of another embodiment of a compartment engagement mechanism, including a hub 3410, a needle cover 3420, two engagement arms 3412, and two needles 3430. Although the illustrated embodiment includes two needles 3430, another number of needles can be used in various embodiments, such as fewer than two needles or more than two needles. In various embodiments, multiple needles can be arranged in another manner than as illustrated. As shown in FIG. 34, the hub 3410 includes guide regions 3414 which receive a portion of the needle cover 3422 and permit the portion of the needle cover 3422 to slide through or along the hub 3410. In the illustrated embodiment, the engagement arms 3412 are integral with a portion of the hub 3410 and are not removable from the hub 3410.

Figure 35:
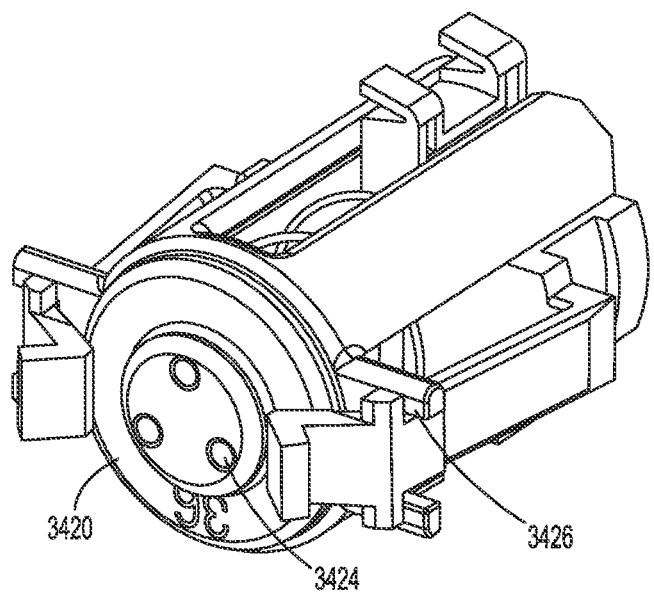
FIG. 35 is another perspective view of the compartment engagement mechanism of FIG. 34, in accordance with aspects of the present disclosure.

FIG. 35 shows another perspective view of the compartment engagement mechanism, including a container-facing end of the mechanism. As shown in FIG. 35, the container-facing end of the needle cover 3420 includes apertures 3424.

The apertures 3424 are aligned with the needles 3430 such that the needles 3430 extend through the apertures 3424 when the needle cover 3420 slides through or along the hub 3410. The needle cover 3420 also includes slots 3426 that receive the engagement arms 3412 of the hub 3410. FIGS. 34 and 35 are exemplary, and variations of or other embodiments of a compartment engagement mechanism are contemplated to be within the scope of the present disclosure.

Figure 36:
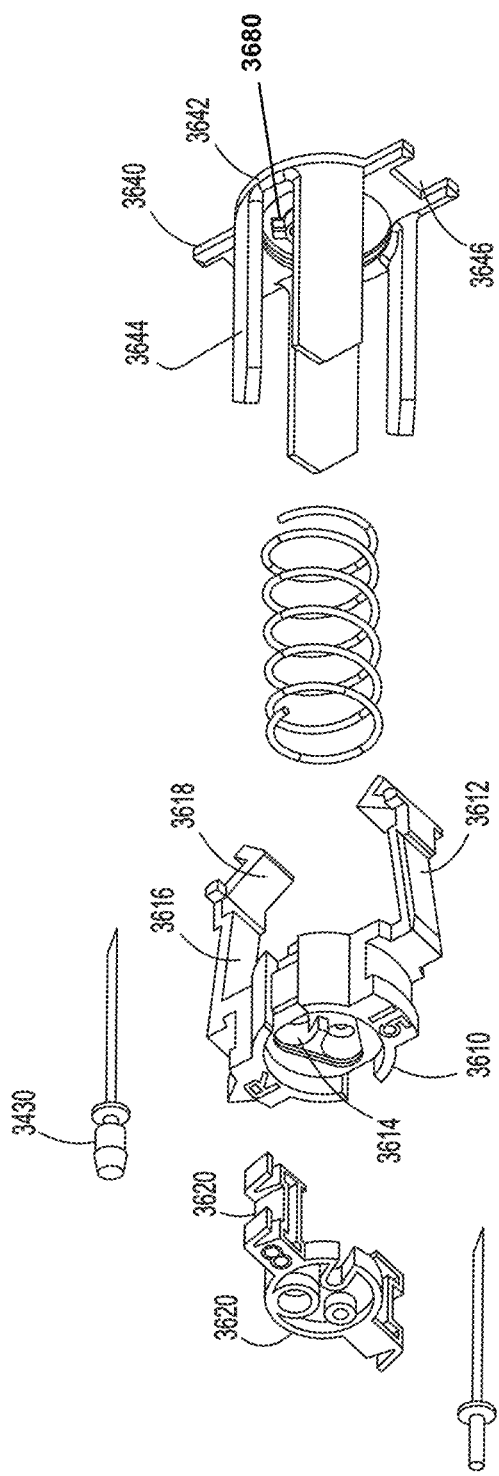
FIG. 36 is a diagram of certain components of the compartment engagement mechanism of FIG. 34, in accordance with aspects of the present disclosure.

FIG. 36 is a diagram of certain components of the container engagement mechanism of FIGS. 34 and 35, including a needle cover 3640, a spring, two hub components 3610, 3620, and two needles 3430. The needles and spring can operate in the same manner described with respect to FIGS. 27-33.

In the illustrated embodiment, the hub is formed from two components 3610, 3620 which combine to form the hub illustrated in FIGS. 34 and 35. In the illustrated embodiment, the engagement arms 3612 are integral with a main hub component 3610 and are not removable from the hub. The main hub component 3610 also includes apertures 3614 for the needles 3430. The other hub component 3620 operates as a needle clamp. In the illustrated embodiment, the needles 3430 are first inserted into the apertures 3614 of the main hub component 3610, and then the other hub component 3620 is fitted onto the needle/hub assembly. In the illustrated embodiment, the other hub component 3620 is structured to clip to the main hub component 3610 and thereby clamp the needles 3630 to the hub. The clip arms 3622 of the other hub component 3620 are oriented perpendicular to the orientation of the engagement arms 3612 of the main hub component 3610. In various embodiments, the two hub components 3610, 3620 may engage each other in other ways, such as by friction fit, for example. In various embodiments, the hub may be formed as one unitary component. In various embodiments, the hub can be made from a plastic material.

Referring again to the main hub component 3610, the engagement arm 3612 includes an elbow portion 3616 and a grasping portion 3618. The grasping portion 3618 of the engagement arm 3612 is connected to the elbow portion 3616. The elbow portion 3616 is semi-flexible so as to flex and permit the grasping portion 3618 to move radially closer to or farther away from the needle cover 3640 of the compartment engagement assembly. The end of the grasping portion 3618 includes a wedge shape pointed towards the needle cover 3640 of the compartment engagement assembly. In various embodiments, the engagement arm 3612 can be made from a plastic material.

In the illustrated embodiment, the needle cover 3640 includes a cap 3642, glide posts 3644 attached to the cap 3642, and slots 3646 that receive the engagement arms 3612 of the hub. In various embodiments, the cap 3642, the slots 3646, and the glide posts 3644 can have various shapes, including shapes different from those illustrated in FIG. 36. In various embodiments, the number of glide posts 3644 can vary, including fewer than four glide posts or more than four glide posts. The glide posts 3644 slide through or along the hub. As shown in FIGS. 34 and 35, each glide post 3644 contacts both of the two hub components 3610, 3620, such that the two hub components 3610, 3620 cooperate to provide guide regions for the glide posts 3644 of the needle cover 3640. In various embodiments, the number of slots 3646 of the needle cover 3640 can correspond to the number of engagement arms 3612. In various embodiments, the needle cover 3640 can be made from a plastic material.

Figure 37:
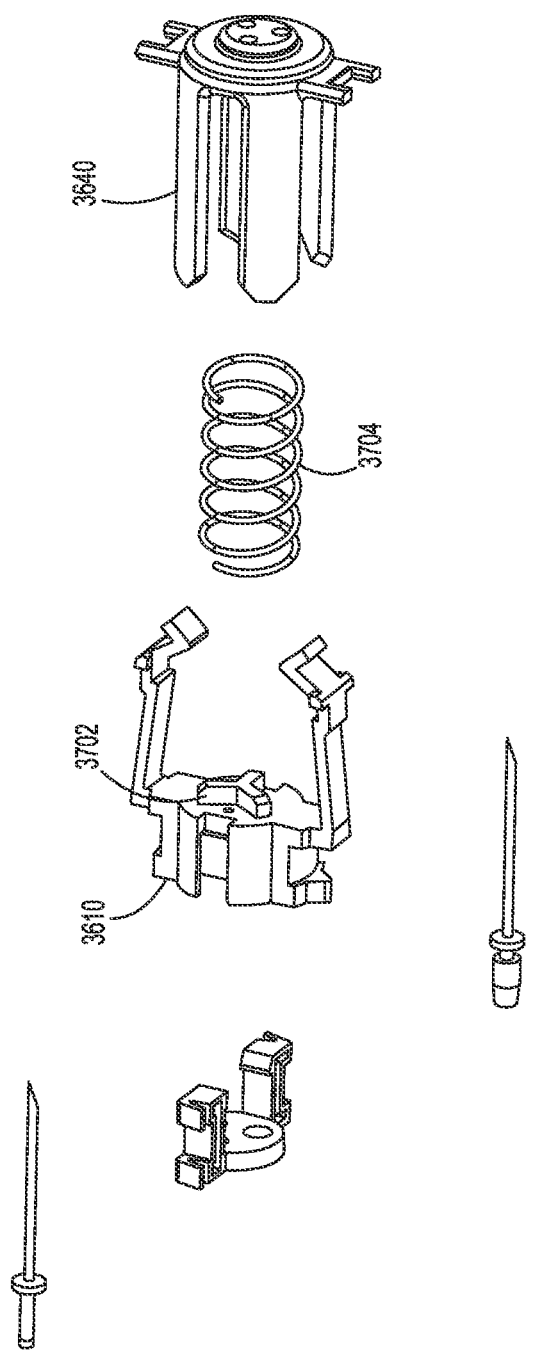
FIG. 37 is another perspective of the components of FIG. 36, in accordance with aspects of the present disclosure.

FIG. 37 shows another perspective of various components shown in FIG. 36. In various embodiments, the hub 3610 can include a spring alignment structure 3702 that operates to align the spring 3704 and also serves as a stop for the retracting needle cover 3640. The shape of the illustrated structure 3702 is exemplary, and other variations are contemplated to be within the scope of the present disclosure. In various embodiments, the needle cover 3640 also includes a spring alignment structure 3680 (shown in FIG. 36), an example of which is partially visible under the cap 3642 in FIG. 36 and which can serve as a dead stop against the spring alignment structure 3702 of the hub 3610. In various embodiments, the spring alignment structure 3680 of the needle cover 3640, if any, can be the same shape as the spring alignment structure 3702 of the hub 3610 or can be a different shape. The illustrated and described embodiments are exemplary, and variations are contemplated to be within the scope of the present disclosure.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in various embodiments," "in some embodiments," "in various embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may be located within a device or system at an end-user location, may be located within a device or system at a manufacturer or servicer location, or may be a cloud computing processor located at a cloud computing provider. The controller may also include a memory to store data and/or instructions that, when executed by the one or more processors, causes the one or more processors to perform one or more methods and/or algorithms.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A container engagement device for engaging a container configured to hold a fluid utilized in a diagnostic process, the container engagement device comprising:
    a hub configured to be fixed in a wall, the hub defining a plurality of guide slots;
    at least one needle secured to the hub and protruding from the hub, the at least one needle configured to puncture the container;
    a needle cover slideably coupled with the hub, the needle cover comprising:
        a cap defining at least one aperture corresponding to the at least one needle, and
        a plurality of glide posts extending from the cap,
        wherein individual glide posts of the plurality of glide posts are positioned at least partially within individual guide slots of the plurality of guide slots of the hub, the plurality of glide posts configured to slide along the plurality of guide slots;
    an engagement arm having a base portion secured to the hub and a grasping portion; and
    a spring positioned between the hub and the cap of the needle cover, the spring having a first compressed state in which the spring pushes the cap against the grasping portion of the engagement arm such that, in the first compressed state of the spring, the grasping portion grasps the cap and maintains the spring in the first compressed state,
    wherein in the first compressed state of the spring, the at least one needle is covered by the cap such that the at least one needle extends from the hub and terminates prior to the at least one aperture of the cap.

2. The container engagement device of claim 1, wherein the spring has a second compressed state in which the spring is more compressed than in the first compressed state, wherein the spring contacts the hub and the cap in the second compressed state.

3. The container engagement device of claim 2, wherein the spring compresses from the first compressed state to the second compressed state by the container pressing against the cap,
    wherein as the spring compresses from the first compressed state to the second compressed state, the spring maintains contact with the hub and the cap.

4. The container engagement device of claim 3, wherein as the spring compresses from the first compressed state to the second compressed state, the grasping portion releases the cap.

5. The container engagement device of claim 2, wherein in the second compressed state of the spring, the at least one needle protrudes through the at least one aperture of the cap.

6. The container engagement device of claim 3, wherein the hub further comprises a spring alignment structure configured to align the spring against the hub, and wherein the cap comprises a spring alignment structure configured to align the spring against the cap.

7. The container engagement device of claim 6, wherein in the second compressed state of the spring, the spring alignment structure of the hub contacts the spring alignment structure of the cap.

8. The container engagement device of claim 4, wherein the spring decompresses from the second compressed state to the first compressed state by the container being moved away from the cap,
    wherein as the spring decompresses from the second compressed state to the first compressed state, the grasping portion re-grasps the cap.

9. The container engagement device of claim 8, wherein as the spring moves between the first compressed state and the second compressed state, the plurality of glide posts of the needle cover slide through the plurality of guide slots of the hub.

10. A system comprising:
    a receptacle configured to receive a container storing a fluid utilized in a diagnostic process, the receptacle having a wall; and
    a container engagement device configured to engage the container, the container engagement device comprising:
        a hub fixed in the wall of the receptacle, the hub defining a plurality of guide slots;
        at least one needle secured to the hub and protruding from the hub, the at least one needle configured to puncture the container;
        a needle cover slideably coupled with the hub, the needle cover comprising:
            a cap defining at least one aperture corresponding to the at least one needle, and
            a plurality of glide posts extending from the cap,
            wherein individual glide posts of the plurality of glide posts are positioned at least partially within individual guide slots of the plurality of guide slots of the hub, the plurality of glide posts configured to slide along the plurality of guide slots;
        an engagement arm having a base portion secured to the hub and a grasping portion; and
        a spring positioned between the hub and the cap of the needle cover, the spring having a first compressed state in which the spring pushes the cap against the grasping portion of the engagement arm such that, in the first compressed state of the spring, the grasping portion grasps the cap and maintains the spring in the first compressed state,
        wherein in the first compressed state of the spring, the at least one needle is covered by the cap such that the at least one needle extends from the hub and terminates prior to the at least one aperture of the cap.

11. The system of claim 10, wherein the spring has a second compressed state in which the spring is more compressed than in the first compressed state, wherein the spring contacts the hub and the cap in the second compressed state.

12. The system of claim 11, wherein the spring compresses from the first compressed state to the second compressed state by the container pressing against the cap,
    wherein as the spring compresses from the first compressed state to the second compressed state, the spring maintains contact with the hub and the cap.

13. The system of claim 12, wherein as the spring compresses from the first compressed state to the second compressed state, the grasping portion releases the cap.

14. The system of claim 11, wherein in the second compressed state of the spring, the at least one needle protrudes through the at least one aperture of the cap.

15. The system of claim 12, wherein the hub further comprises a spring alignment structure configured to align the spring against the hub, and
   wherein the cap comprises a spring alignment structure configured to align the spring against the cap.

16. The system of claim 15, wherein in the second compressed state of the spring, the spring alignment structure of the hub contacts the spring alignment structure of the cap.

17. The system of claim 13, wherein the spring decompresses from the second compressed state to the first compressed state by the container being moved away from the cap,
   wherein as the spring decompresses from the second compressed state to the first compressed state, the grasping portion re-grasps the cap.

18. The system of claim 17, wherein as the spring moves between the first compressed state and the second compressed state, the plurality of glide posts of the needle cover slide through the plurality of guide slots of the hub.

* * * * *